(12) United States Patent
Besaw et al.

(10) Patent No.: US 12,427,036 B2
(45) Date of Patent: Sep. 30, 2025

(54) EXPANDABLE IMPLANTS

(71) Applicant: NuVasive, Inc., San Diego, CA (US)

(72) Inventors: Christopher Besaw, San Diego, CA (US); Thomas Sweeney, San Diego, CA (US); Scott Uyekawa, San Diego, CA (US); Garrett Mikels, San Diego, CA (US); Steven Lillig, San Diego, CA (US)

(73) Assignee: NuVasive, Inc., San Diego, CA (US)

( * ) Notice: Subject to any disclaimer, the term of this patent is extended or adjusted under 35 U.S.C. 154(b) by 149 days.

(21) Appl. No.: 17/657,679

(22) Filed: Apr. 1, 2022

(65) Prior Publication Data

US 2022/0313449 A1 Oct. 6, 2022

Related U.S. Application Data

(60) Provisional application No. 63/249,129, filed on Sep. 28, 2021, provisional application No. 63/170,570, filed on Apr. 5, 2021, provisional application No. 63/170,532, filed on Apr. 4, 2021.

(51) Int. Cl.
*A61F 2/44* (2006.01)
*A61F 2/30* (2006.01)

(52) U.S. Cl.
CPC .... *A61F 2/447* (2013.01); *A61F 2002/30405* (2013.01); *A61F 2002/30484* (2013.01); *A61F 2002/30538* (2013.01); *A61F 2002/30556* (2013.01)

(58) Field of Classification Search
CPC ...... A61F 2/44–447; A61F 2002/30405; A61F 2002/30484; A61F 2002/30538; A61F 2002/30556
See application file for complete search history.

(56) References Cited

U.S. PATENT DOCUMENTS

| 5,554,191 | A  | 9/1996 | Lahille et al. |
| 5,865,848 | A  | 2/1999 | Baker |
| 6,045,579 | A  | 4/2000 | Hochshuler et al. |
| 6,136,031 | A  | 10/2000 | Middleton |
| 6,176,882 | B1 | 1/2001 | Biedermann et al. |

(Continued)

FOREIGN PATENT DOCUMENTS

| CN | 100584283 C | 1/2010 |
| EP | 2226039 A1 | 9/2010 |

(Continued)

OTHER PUBLICATIONS

International Search Report and Written Opinion, International Application No. PCT/US2022/023048, dated Jul. 22, 2022, 15 pages.

*Primary Examiner* — Nicholas J Plionis

(57) ABSTRACT

An expandable implant includes: a first endplate, a second endplate, a first translating member moveably coupled to a first actuator, and a second translating member moveably coupled to a second actuator. The first translating member may be configured to move independently from the second translating member, and the first translating member and the second translating member may be configured to change a spatial relationship between the first endplate and the second endplate. The change in spatial relationship may change a resulting height, length, width, angle of lordosis, or other dimension of the expandable implant.

14 Claims, 24 Drawing Sheets

(56) References Cited

U.S. PATENT DOCUMENTS

| | | |
|---|---|---|
| 6,395,035 B2 | 5/2002 | Bresina et al. |
| 6,436,142 B1 | 8/2002 | Paes et al. |
| 6,443,990 B1 | 9/2002 | Aebi et al. |
| 6,451,057 B1 | 9/2002 | Chen et al. |
| 6,719,796 B2 | 4/2004 | Cohen et al. |
| 6,821,298 B1 | 11/2004 | Jackson |
| 7,128,760 B2 | 10/2006 | Michelson |
| 7,217,291 B2 | 5/2007 | Zucherman et al. |
| 7,763,028 B2 | 7/2010 | Lim et al. |
| 7,819,921 B2 | 10/2010 | Grotz |
| 7,837,734 B2 | 11/2010 | Zucherman et al. |
| 7,985,256 B2 | 7/2011 | Grotz et al. |
| 8,105,382 B2 | 1/2012 | Olmos et al. |
| 8,398,713 B2 | 3/2013 | Weiman |
| 8,435,298 B2 | 5/2013 | Weiman |
| 8,454,617 B2 | 6/2013 | Schaller et al. |
| 8,465,547 B2 | 6/2013 | Melkent et al. |
| 8,491,659 B2 | 7/2013 | Weiman |
| 8,496,706 B2 | 7/2013 | Ragab et al. |
| 8,568,481 B2 | 10/2013 | Olmos et al. |
| 8,628,578 B2 | 1/2014 | Miller et al. |
| 8,632,595 B2 | 1/2014 | Weiman |
| 8,679,161 B2 | 3/2014 | Malandain et al. |
| 8,795,366 B2 | 8/2014 | Varela |
| 8,845,731 B2 | 9/2014 | Weiman |
| 8,845,732 B2 | 9/2014 | Weiman |
| 8,845,734 B2 | 9/2014 | Weiman |
| 8,894,711 B2 | 11/2014 | Varela |
| 8,894,712 B2 | 11/2014 | Varela |
| 8,940,049 B1 | 1/2015 | Jimenez et al. |
| 9,039,771 B2 | 5/2015 | Glerum et al. |
| 9,125,757 B2 | 9/2015 | Weiman |
| 9,220,610 B2 | 12/2015 | Chen |
| 9,233,007 B2 | 1/2016 | Sungarian et al. |
| 9,314,348 B2 | 4/2016 | Emstad |
| 9,320,610 B2 | 4/2016 | Alheidt et al. |
| 9,358,129 B2 | 6/2016 | Weiman |
| 9,364,339 B2 | 6/2016 | Mayer |
| 9,370,434 B2 | 6/2016 | Weiman |
| 9,402,739 B2 | 8/2016 | Weiman et al. |
| 9,445,919 B2 | 9/2016 | Palmatier et al. |
| 9,486,328 B2 | 11/2016 | Jimenez et al. |
| 9,492,288 B2 | 11/2016 | Wagner et al. |
| 9,522,070 B2 | 12/2016 | Flower et al. |
| 9,561,116 B2 | 2/2017 | Weiman et al. |
| 9,585,766 B2 | 3/2017 | Robinson |
| 9,585,767 B2 | 3/2017 | Robinson |
| 9,622,878 B2 | 4/2017 | Grotz |
| 9,662,224 B2 | 5/2017 | Weiman et al. |
| 9,668,876 B2 | 6/2017 | Blain et al. |
| 9,668,879 B2 | 6/2017 | Jimenez et al. |
| 9,713,536 B2 | 7/2017 | Foley et al. |
| 9,717,601 B2 | 8/2017 | Miller |
| 9,750,618 B1 | 9/2017 | Daffinson et al. |
| 9,795,493 B1 | 10/2017 | Bannigan |
| 9,801,733 B2 | 10/2017 | Wolters et al. |
| 9,801,734 B1 | 10/2017 | Stein et al. |
| 9,839,528 B2 | 12/2017 | Weiman et al. |
| 9,855,151 B2 | 1/2018 | Weiman |
| 9,861,494 B2 | 1/2018 | Grotz |
| 9,872,778 B2 | 1/2018 | Grotz |
| 9,931,226 B2 | 4/2018 | Kurtaliaj et al. |
| 9,956,087 B2 | 5/2018 | Seifert et al. |
| 9,962,270 B2 | 5/2018 | Alheidt et al. |
| 9,962,272 B1 | 5/2018 | Daffinson et al. |
| 9,987,144 B2 | 6/2018 | Seifert et al. |
| 9,999,515 B1 | 6/2018 | Grotz |
| 10,022,239 B1 | 7/2018 | Lentner et al. |
| 10,034,765 B2 | 7/2018 | Blain et al. |
| 10,034,769 B2 | 7/2018 | Baynham |
| 10,039,650 B2 | 8/2018 | Lamborne et al. |
| 10,052,214 B2 | 8/2018 | Jimenez et al. |
| 10,076,423 B2 | 9/2018 | Miller et al. |
| 10,085,846 B2 | 10/2018 | Grotz |
| 10,098,757 B2 | 10/2018 | Logan et al. |
| 10,111,758 B2 | 10/2018 | Robinson |
| 10,154,911 B2 | 12/2018 | Predick et al. |
| 10,154,914 B2 | 12/2018 | Robinson |
| 10,172,718 B2 | 1/2019 | Wolters et al. |
| 10,195,050 B2 | 2/2019 | Palmatier et al. |
| 10,226,356 B2 | 3/2019 | Grotz |
| 10,238,503 B2 | 3/2019 | Branch et al. |
| 10,278,830 B1 | 5/2019 | Walker et al. |
| 10,278,831 B2 | 5/2019 | Sandul |
| 10,285,819 B2 | 5/2019 | Greenhalgh |
| 10,285,820 B2 | 5/2019 | Greenhalgh |
| 10,285,824 B2 | 5/2019 | Robinson |
| 10,292,828 B2 | 5/2019 | Greenhalgh |
| 10,292,830 B2 | 5/2019 | McLuen et al. |
| 10,299,934 B2 | 5/2019 | Seifert et al. |
| 10,314,719 B2 | 6/2019 | Hessler et al. |
| 10,322,011 B2 | 6/2019 | Baynham |
| 10,327,917 B2 | 6/2019 | Glerum et al. |
| 10,350,081 B2 | 7/2019 | Seifert et al. |
| 10,350,084 B1 | 7/2019 | Lin et al. |
| 10,350,085 B2 | 7/2019 | Glerum et al. |
| 10,363,142 B2 | 7/2019 | McClintock et al. |
| 10,369,004 B2 | 8/2019 | Faulhaber |
| 10,369,010 B2 | 8/2019 | Robinson et al. |
| 10,376,377 B2 | 8/2019 | Seifert et al. |
| 10,383,741 B2 | 8/2019 | Butler et al. |
| 10,390,960 B2 | 8/2019 | Bannigan et al. |
| 10,390,962 B2 | 8/2019 | Weiman |
| 10,390,963 B2 | 8/2019 | Olmos et al. |
| 10,398,563 B2 | 9/2019 | Engstrom |
| 10,398,566 B2 | 9/2019 | Olmos et al. |
| 10,398,567 B2 | 9/2019 | Robinson |
| 10,413,421 B2 | 9/2019 | Amold et al. |
| 10,413,422 B2 | 9/2019 | Flower et al. |
| 10,420,654 B2 | 9/2019 | Logan et al. |
| 10,426,632 B2 | 10/2019 | Butler et al. |
| 10,441,430 B2 | 10/2019 | Ludwig et al. |
| 10,449,056 B2 | 10/2019 | Cain |
| 10,492,924 B2 | 12/2019 | Stein et al. |
| 10,500,064 B2 | 12/2019 | Robinson |
| 10,507,116 B2 | 12/2019 | Shoshtaev |
| 10,512,550 B2 | 12/2019 | Bechtel et al. |
| 10,524,924 B2 | 1/2020 | Davenport et al. |
| 10,531,964 B2 | 1/2020 | Miller et al. |
| 10,575,964 B2 | 3/2020 | Robinson |
| 10,575,966 B2 | 3/2020 | Logan et al. |
| 10,583,015 B2 | 3/2020 | Olmos et al. |
| 10,610,376 B2 | 4/2020 | Kuyler et al. |
| 10,610,377 B2 | 4/2020 | Baynham |
| 10,617,533 B2 | 4/2020 | Glerum et al. |
| 10,624,761 B2 | 4/2020 | Davenport et al. |
| 10,631,998 B2 | 4/2020 | Wu et al. |
| 10,639,166 B2 | 5/2020 | Weiman et al. |
| 10,646,351 B2 | 5/2020 | Blain et al. |
| 10,667,927 B2 | 6/2020 | Lamborne et al. |
| 10,682,239 B2 | 6/2020 | Hsu et al. |
| 10,682,241 B2 | 6/2020 | Glerum et al. |
| 10,687,963 B2 | 6/2020 | Jimenez et al. |
| 10,973,650 B2 | 4/2021 | Stein |
| 11,234,833 B2 | 2/2022 | Brotman et al. |
| 11,273,047 B2 | 3/2022 | Besaw et al. |
| 2002/0045945 A1 | 4/2002 | Liu et al. |
| 2004/0087947 A1 | 5/2004 | Lim et al. |
| 2006/0247781 A1 | 11/2006 | Francis et al. |
| 2009/0222100 A1 | 9/2009 | Cipoletti et al. |
| 2009/0292361 A1 | 11/2009 | Lopez |
| 2010/0145455 A1 | 6/2010 | Simpson et al. |
| 2011/0015742 A1 | 1/2011 | Hong |
| 2011/0112644 A1 | 5/2011 | Zilberstein et al. |
| 2011/0160861 A1 | 6/2011 | Jimenez et al. |
| 2013/0197642 A1* | 8/2013 | Ernst .................. A61F 2/442 623/17.16 |
| 2013/0231747 A1 | 9/2013 | Olmos et al. |
| 2014/0236296 A1 | 8/2014 | Wagner et al. |
| 2014/0236297 A1 | 8/2014 | Iott et al. |
| 2015/0272743 A1 | 10/2015 | Jimenez et al. |
| 2015/0374508 A1 | 12/2015 | Sandul |
| 2016/0022434 A1 | 1/2016 | Robinson |
| 2016/0166396 A1 | 6/2016 | McClintock |

(56) References Cited

U.S. PATENT DOCUMENTS

| | | | |
|---|---|---|---|
| 2016/0235548 A1* | 8/2016 | McLaughlin | A61F 2/4684 |
| 2016/0256291 A1 | 9/2016 | Miller | |
| 2017/0105844 A1* | 4/2017 | Kuyler | A61F 2/4611 |
| 2017/0112630 A1 | 4/2017 | Kuyler et al. | |
| 2017/0119542 A1 | 5/2017 | Logan et al. | |
| 2017/0135824 A1 | 5/2017 | Suddaby et al. | |
| 2017/0143507 A1 | 5/2017 | Flower et al. | |
| 2017/0151065 A1 | 6/2017 | Warren et al. | |
| 2017/0216049 A1 | 8/2017 | Grotz | |
| 2017/0224504 A1 | 8/2017 | Butler et al. | |
| 2017/0224505 A1 | 8/2017 | Butler et al. | |
| 2017/0231780 A1 | 8/2017 | D'Urso | |
| 2017/0281358 A1 | 10/2017 | Wagner et al. | |
| 2017/0290674 A1 | 10/2017 | Olmos et al. | |
| 2017/0290675 A1 | 10/2017 | Olmos et al. | |
| 2017/0290676 A1 | 10/2017 | Olmos et al. | |
| 2017/0290677 A1 | 10/2017 | Olmos et al. | |
| 2017/0290678 A1 | 10/2017 | Olmos et al. | |
| 2017/0333198 A1 | 11/2017 | Robinson | |
| 2018/0036138 A1 | 2/2018 | Robinson | |
| 2018/0064551 A1 | 3/2018 | Stein et al. | |
| 2018/0147065 A1 | 5/2018 | Daffinson et al. | |
| 2018/0147066 A1 | 5/2018 | Daffinson et al. | |
| 2018/0161171 A1 | 6/2018 | Frasier et al. | |
| 2018/0161175 A1 | 6/2018 | Frasier et al. | |
| 2018/0193160 A1 | 7/2018 | Hsu et al. | |
| 2018/0296361 A1 | 10/2018 | Butler et al. | |
| 2018/0303625 A1 | 10/2018 | Alheidt et al. | |
| 2018/0318101 A1* | 11/2018 | Engstrom | A61F 2/4425 |
| 2018/0333273 A1 | 11/2018 | Blain et al. | |
| 2018/0360615 A1 | 12/2018 | Miller et al. | |
| 2019/0008649 A1 | 1/2019 | Logan et al. | |
| 2019/0008657 A1 | 1/2019 | Lamborne et al. | |
| 2019/0021868 A1 | 1/2019 | Ludwig et al. | |
| 2019/0021870 A1 | 1/2019 | Jimenez et al. | |
| 2019/0021872 A1 | 1/2019 | Robinson | |
| 2019/0133780 A1 | 5/2019 | Matthews et al. | |
| 2019/0133788 A1 | 5/2019 | Weiman et al. | |
| 2019/0142602 A1 | 5/2019 | Olmos et al. | |
| 2019/0151110 A1 | 5/2019 | Faulhaber | |
| 2019/0201209 A1 | 7/2019 | Branch et al. | |
| 2019/0231552 A1 | 8/2019 | Sandul | |
| 2019/0240039 A1 | 8/2019 | Walker et al. | |
| 2019/0240043 A1 | 8/2019 | Greenhalgh | |
| 2019/0274837 A1 | 9/2019 | Eisen et al. | |
| 2019/0274838 A1 | 9/2019 | Manwill et al. | |
| 2019/0290447 A1 | 9/2019 | Stein | |
| 2019/0314168 A1 | 10/2019 | Faulhaber | |
| 2019/0321190 A1 | 10/2019 | Wagner et al. | |
| 2019/0321191 A1 | 10/2019 | Glerum et al. | |
| 2019/0321198 A1 | 10/2019 | Glerum et al. | |
| 2019/0328540 A1 | 10/2019 | Seifert et al. | |
| 2019/0336301 A1 | 11/2019 | Engstrom | |
| 2019/0336302 A1 | 11/2019 | Seifert et al. | |
| 2019/0358051 A1 | 11/2019 | Flower et al. | |
| 2019/0374348 A1 | 12/2019 | Butler et al. | |
| 2020/0008951 A1 | 1/2020 | McClintock et al. | |
| 2020/0030114 A1 | 1/2020 | Cain | |
| 2020/0085586 A1 | 3/2020 | Ludwig et al. | |
| 2020/0093607 A1 | 3/2020 | Davenport et al. | |
| 2020/0093609 A1 | 3/2020 | Shoshtaev | |
| 2020/0100904 A1 | 4/2020 | Stein et al. | |
| 2020/0113706 A1 | 4/2020 | Robinson | |
| 2020/0129306 A1 | 4/2020 | Miller et al. | |
| 2020/0129307 A1 | 4/2020 | Hunziker et al. | |
| 2020/0281741 A1 | 9/2020 | Grotz | |
| 2021/0275317 A1* | 9/2021 | Spetzger | A61F 2/44 |

FOREIGN PATENT DOCUMENTS

| | | |
|---|---|---|
| EP | 3482723 A1 | 5/2019 |
| JP | 2000210315 A | 8/2000 |
| JP | 2008054710 A | 3/2008 |
| KR | 100900991 B1 | 6/2009 |
| KR | 100905962 B1 | 7/2009 |
| RU | 2460499 C2 | 9/2012 |
| WO | 2009/126968 A1 | 10/2009 |
| WO | 2019/006407 A1 | 1/2019 |

* cited by examiner

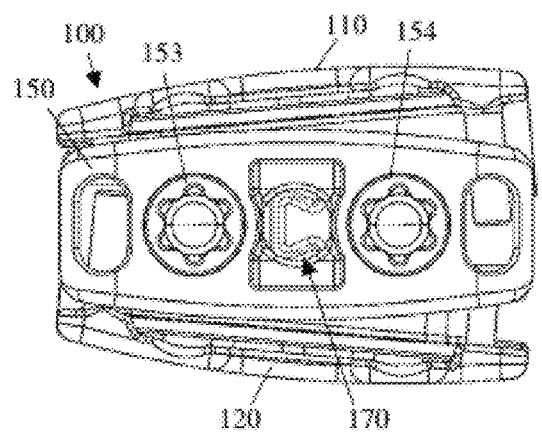
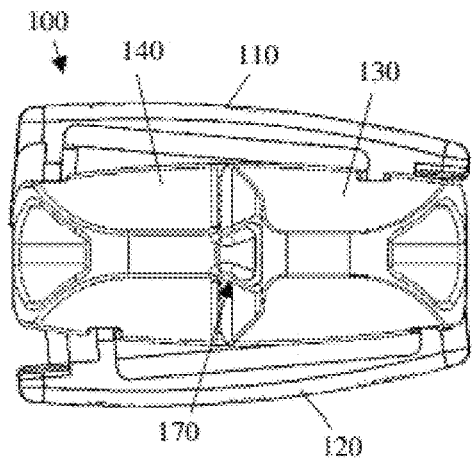
FIG. 14    FIG. 15
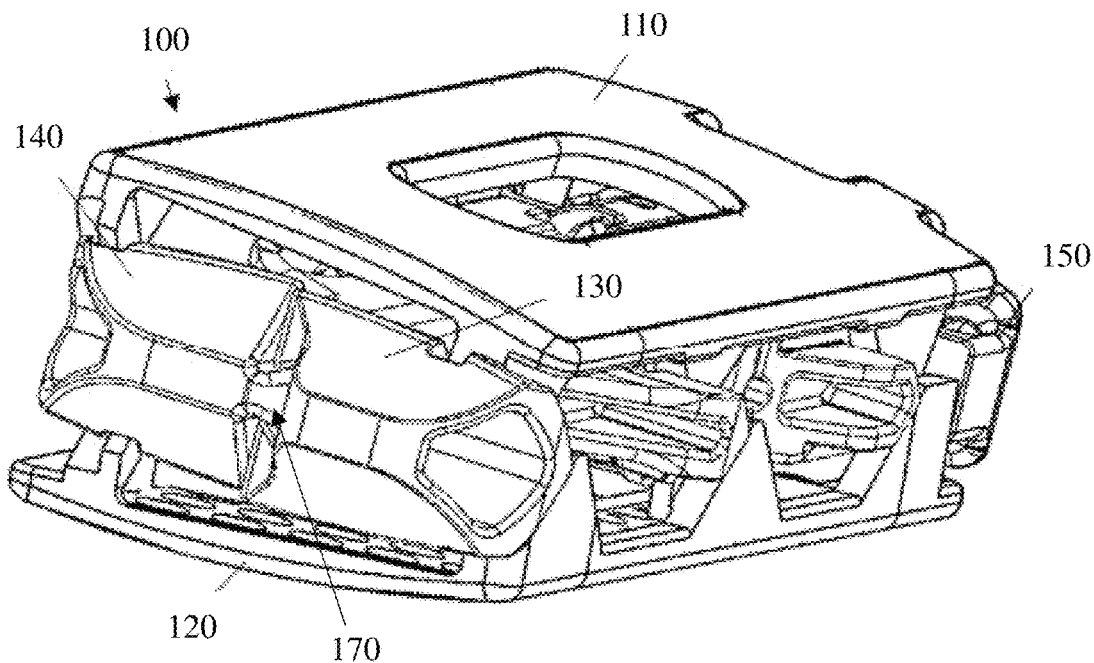
FIG. 16

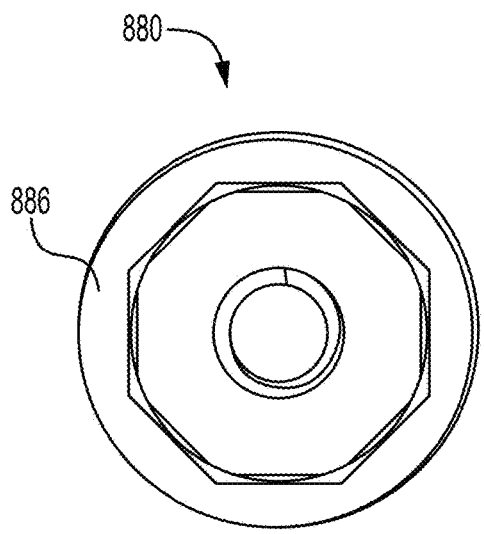
FIG. 43
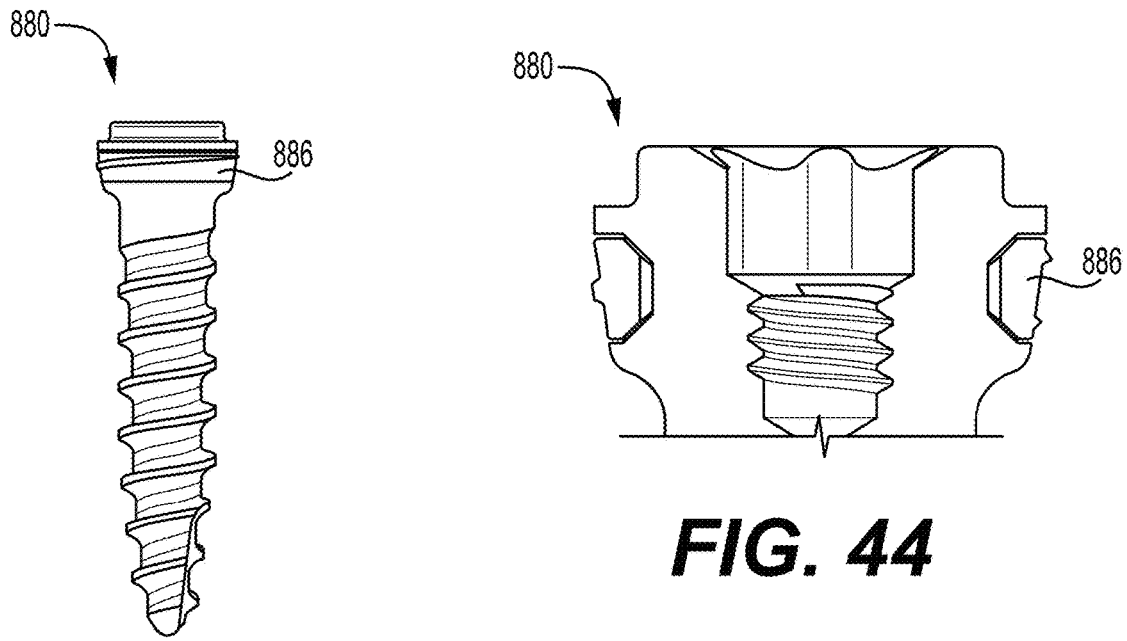
FIG. 44
FIG. 45
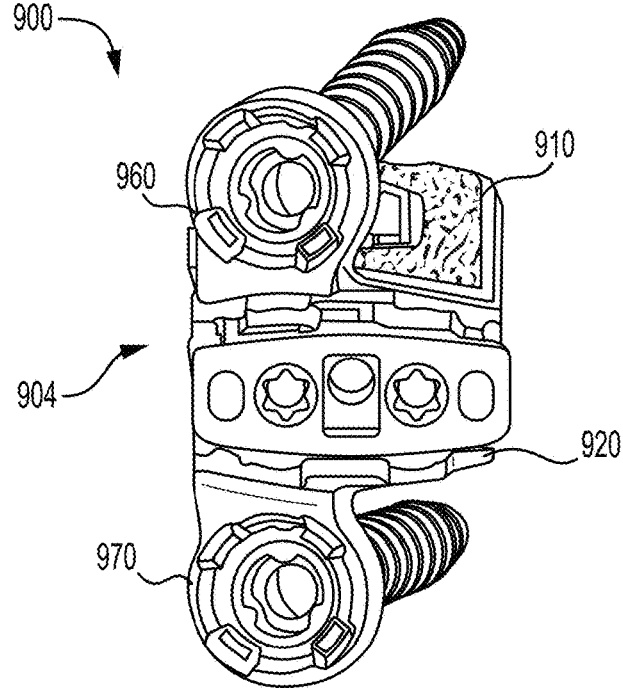
FIG. 46

EXPANDABLE IMPLANTS

CROSS REFERENCE TO RELATED APPLICATIONS

The present patent application claims priority to U.S. Provisional Patent Application No. 63/170,532, filed Apr. 4, 2021; U.S. Provisional Patent Application No. 63/170,570, filed Apr. 5, 2021; and U.S. Provisional Patent Application No. 63/249,129, filed Sep. 28, 2021.

BACKGROUND OF THE INVENTION

Field of the Invention

The present disclosure relates generally to medical implants, and more particularly to expandable implants.

Description of the Related Art

Back problems are one of the most common and debilitating occurrences in people of all ethnicities. In the United States alone, over 500,000 spine lumbar and cervical fusion procedures are performed each year. One of the causes of back pain and disability results from the rupture or degeneration of one or more intervertebral discs in the spine.

Surgical procedures are commonly performed to correct problems with displaced, damaged, or degenerated intervertebral discs due to trauma, disease or aging. Generally, spinal fusion procedures involve removing some or all of the diseased or damaged disc, and inserting one or more intervertebral implants into the resulting disc space. Anterior lumbar interbody fusion (ALIF) and lateral lumbar interbody fusion procedures are two of the techniques that spine surgeons use to access the portions of the spine to be repaired or replaced.

Replacement of injured or deteriorated spinal bone with artificial implants involves understanding and consideration of the mechanisms of the stresses inherent in the spine, as well as the biological properties of the body in response to the devices. Further, the size, configuration, and placement of an artificial implant involve precision positioning and handling by a skilled surgeon.

SUMMARY OF THE INVENTION

This disclosure includes expandable implant devices and methods for using the same. The expandable implant device may be adjusted to form a particular height and/or a particular lordosis angle, as influenced by, inter alia, the needs or requirements of the patient, the target procedure of a surgeon, and may incorporate various features to accommodate spinal fusion.

In some embodiments, an expandable implant includes: a first endplate, a second endplate, a first translating member moveably coupled to a first actuator, and a second translating member moveably coupled to a second actuator. The first translating member may be configured to move independently from the second translating member, and the first translating member and the second translating member may be configured to change a spatial relationship between the first endplate and the second endplate. The spatial relationship may define a height, length, width, angle of lordosis, or any other dimension of the expandable implant.

In some embodiments, an expandable implant includes: a first endplate, a second endplate, a first translating member disposed between the first endplate and the second endplate and moveably coupled to a first drive screw, and a second translating member disposed between the first endplate and the second endplate and moveably coupled to a second drive screw. The first translating member is configured to move independently from the second translating member, and the first translating member and the second translating member are configured to change a spatial relationship between the first endplate and the second endplate.

In some embodiments, anti-migration features are provided to restrict undesired rotation of the lead screws. The anti-migration features provide added rigidity and increase an amount of load the expandable implant is configured to support.

In some embodiments, the first translating member and the second translating member may be moveably coupled at the distal end of the expandable implant by a dovetail coupling. Similarly, in some embodiments, the first translating member and the second translating member may be moveably coupled at the proximal end of the expandable implant by a dovetail coupling slideably coupling a first actuator housing to a second actuator housing.

In one embodiment of a method is provided for treating a spinal condition using an expandable implant, the method including the steps of: accessing an intervertebral disc space via a generally lateral approach, inserting an expandable implant into the intervertebral disc space, the expandable implant having a first translating member moveably coupled to a first actuator and a second translating member moveably coupled to a second actuator, with the first translating member and the second translating member configured to change a spatial relationship between the first endplate and the second endplate as they move, and actuating at least one of the first actuator and the second actuator to change the spatial relationship between the first endplate and the second endplate to change a dimension of the expandable implant.

BRIEF DESCRIPTION OF THE DRAWINGS

These and other features will be further understood by those with skill in the art upon a review of the appended drawings, wherein:

FIG. 14 shows a rear view of the expandable implant in accordance with the first embodiment adjusted to an exemplary angle of lordosis;

FIG. 15 shows a front view of the expandable implant in accordance with the first embodiment adjusted to an exemplary angle of lordosis;

FIG. 16 shows a perspective view of the expandable implant in accordance with the first embodiment adjusted to an exemplary angle of lordosis;

FIG. 43 shows a side view of a fixation element according to another embodiment;

FIG. 44 shows a cross-sectional view of the head of the fixation element according to the embodiment of FIG. 43;

FIG. 45 shows a top-down view of the fixation element according the embodiment of FIG. 43;

FIG. 46 shows a rear view of an expandable implant in accordance with an eighth embodiment;

DETAILED DESCRIPTION

For purposes of explanation and not limitation, details and descriptions of certain preferred embodiments are hereinafter provided such that one having ordinary skill in the art may be enabled to make and use the invention. These details and descriptions are representative only of certain preferred embodiments. However, a myriad of other embodiments which will not be expressly described will be readily understood by those having skill in the art upon a thorough review hereof. Accordingly, any reviewer of the instant disclosure should interpret the scope of the invention by the claims, and such scope shall not be limited by the embodiments described and illustrated herein.

This disclosure includes expandable implant devices and methods for using the same. The expandable implant device may be adjusted to form a particular height and a particular lordosis angle, as influenced by: the needs or requirements of the patient, the target procedure of a surgeon, etc., and the expandable implant may further incorporate various features to accommodate and/or promote spinal fusion.

In a general embodiment, an expandable implant includes: a first endplate, a second endplate, a first translating member, and a second translating member, wherein the first translating member is configured to move independently of the second translating member, and wherein movement of at least one of the first translating member and the second translating member is configured to change a dimension of the expandable implant.

In some embodiments, an expandable implant includes: a first endplate, a second endplate, a first actuator having a first translating member moveably coupled to the first actuator, and a second actuator having a second translating member moveably coupled to the second actuator with the first translating member configured to move independently from the second translating member, and the first translating member and the second translating member configured to change a spatial relationship between the first endplate and the second endplate. The spatial relationship may include a dimension of the expandable implant, and may include at least one of height, width, length, lordosis, and any other dimension of the expandable implant.

Now turning to the drawings, FIG. 1-13 show various views of an expandable implant 100 in accordance with a first embodiment.

Figure 1:
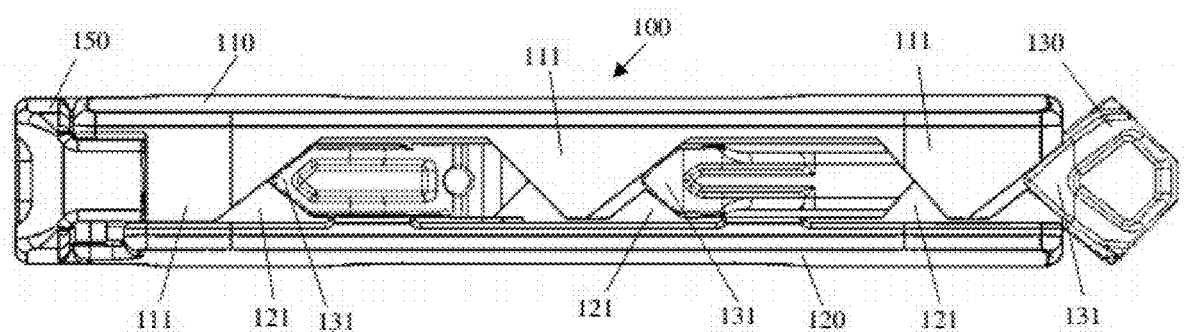
FIG. 1 shows a side view of the expandable implant in accordance with the first embodiment, in which the expandable implant is collapsed in a first configuration.

FIG. 1 shows an expandable implant 100 collapsed in a first configuration. Expandable implant 100 is shown including a first endplate 110, a second endplate 120, a first translating member 130 (FIGS. 5-8) and a second actuator having a second translating member 140 (FIGS. 5-8). First translating member 130 may be configured to move independently from second translating member 140, and first translating member 130 and second translating member 140 may be configured to change a spatial relationship between first endplate 110 and second endplate 120.

Figure 3:
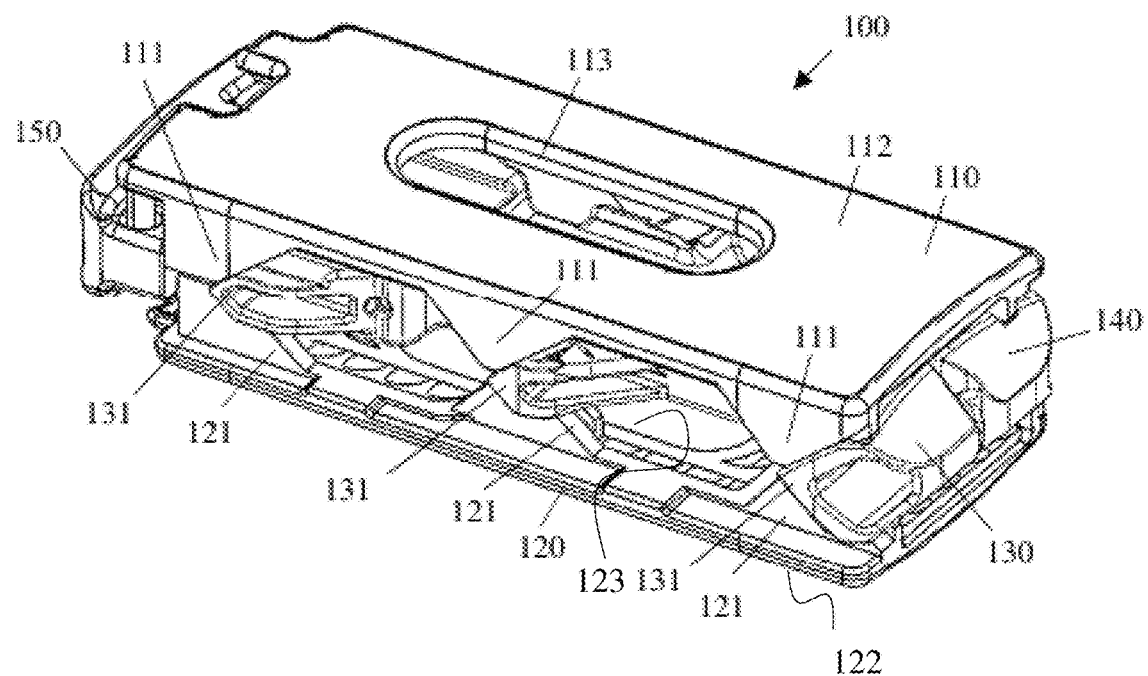
FIG. 3 shows a front perspective view of the expandable implant in accordance with the first embodiment, in which the expandable implant is expanded in a second configuration.

The expandable implant 100 may be inserted through an access incision in a collapsed configuration to reduce an insertion profile of expandable implant 100. The first endplate 110 and the second endplate 120 further include a fusion aperture 113 (FIGS. 3-5), 123 (FIG. 3) and a bone contact surface 112 (FIGS. 3-5), 122 (FIG. 3). After placing the expandable implant 100 within a prepared intervertebral disc space of a patient, and adjusting the expandable implant 100 to a desired height and angle of lordosis, the bone contact surfaces 112, 122 of the first endplate 110 and the second endplate 120, respectively, are configured to contact an inferior vertebral body and a superior vertebral body respectively. As such, the bone contact surfaces 112, 122 may further include anti-migration features configured to prevent slippage of the expandable implant 100 within the intervertebral disc space of the patient. The bone contact surfaces 112, 122 may further include a porous bone contact surface to promote fusion.

Figure 2:
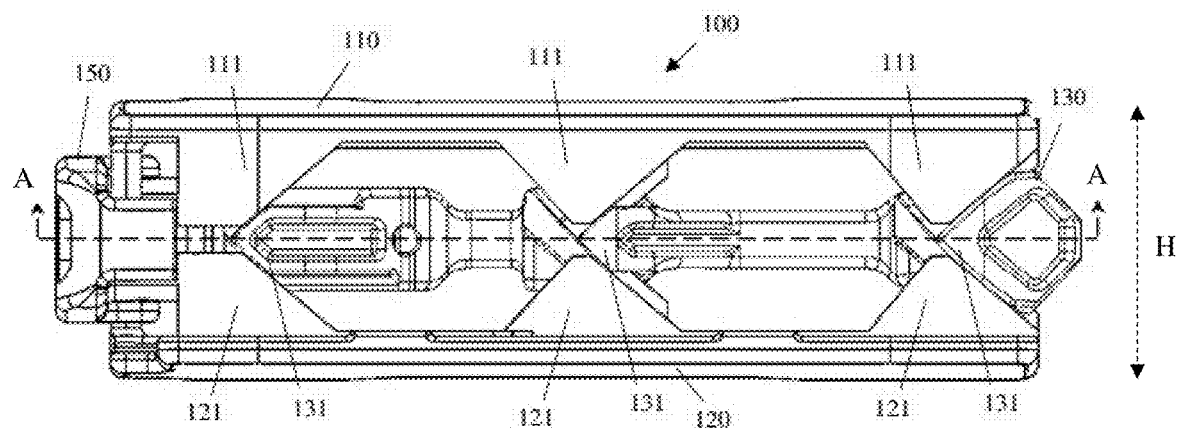
FIG. 2 shows a side view of the expandable implant in accordance with the first embodiment, in which the expandable implant is expanded in a second configuration.
Figure 6:
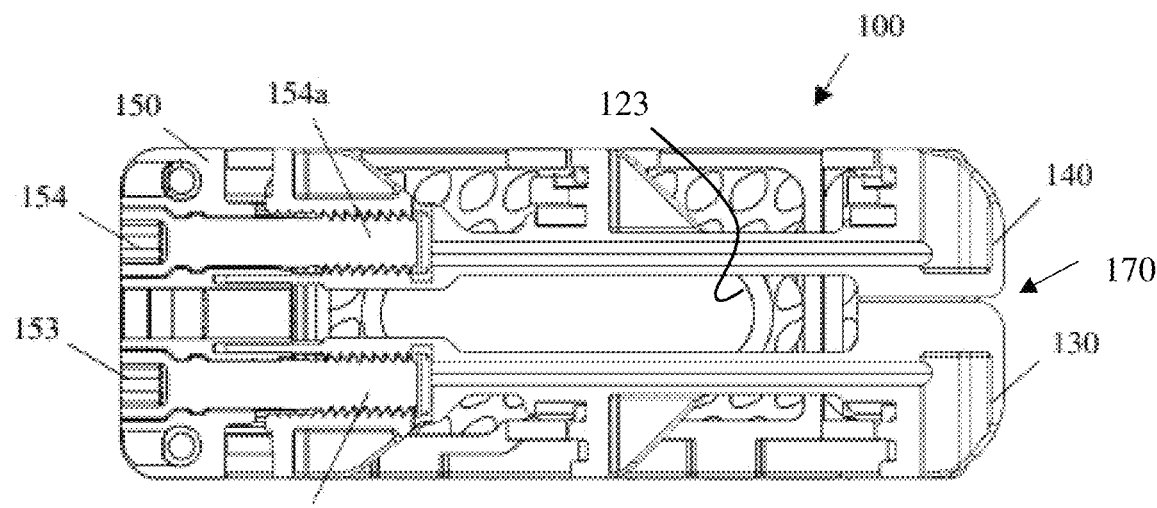
FIG. 6 shows a cross-sectional top view of the expandable implant in accordance with the first embodiment.
Figure 7:
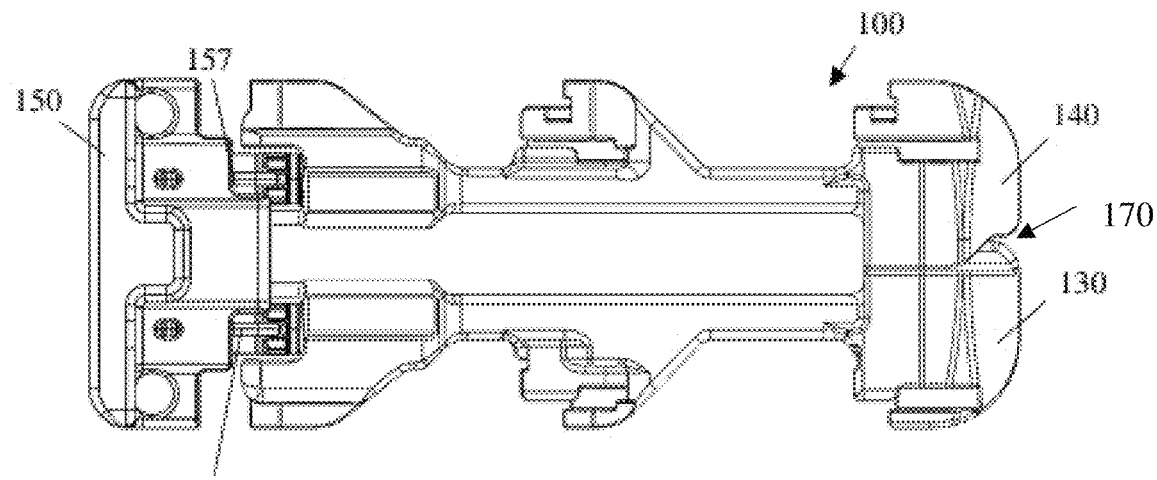
FIG. 7 shows a top view of an expansion mechanism of the expandable implant in accordance with the first embodiment.
Figure 9:
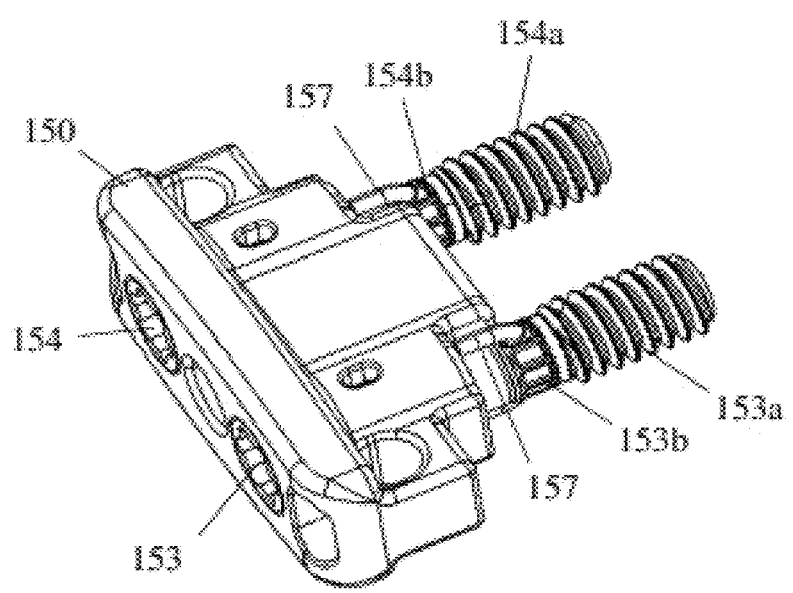
FIG. 9 shows a perspective view of an actuator housing of an expandable implant in accordance with the first embodiment.

FIG. 2 shows a side view of the expandable implant 100 expanded in a second configuration, to a height H. Here, and as described above, the threaded portion of the first drive screw 153 (FIGS. 6 and 9) and the threaded portion of the second drive screw 154 (FIGS. 6 and 9) have been driven into the threaded cavity of the first translating member 130 and the threaded cavity of the second translating member 140 respectively. Communication of the threaded portion 153a (FIGS. 6 and 9) of the first drive screw 153 with the threaded cavity of the first translating member 130 moves the first threaded portion towards the actuator housing 150 (FIGS. 6-7 and 9). Similarly, communication of the threaded portion 154a of the second drive screw 154 with the threaded cavity of the second translating member 140 moves the second threaded portion towards the actuator housing 150.

FIG. 3 shows a front perspective view of the expandable implant 100 in accordance with the first embodiment. Here, the expandable implant 100 is shown in the second, expanded configuration. Rotation of the first drive screw 153 may drive the threaded portion 153a of the first drive screw 153 into the threaded cavity of the first translating member 130. The position of the first drive screw 153 relative to the actuator housing 150 may be fixed, with the drive screw 153 captured but rotatably disposed about the actuator housing 150. Driving the threaded portion 153a of the first drive screw 153 into the translating member 130 effectively moves the translating member 130 along the length of the first drive screw 153 toward the actuator housing 150, changing a dimension of the expandable implant 100.

Figure 4:
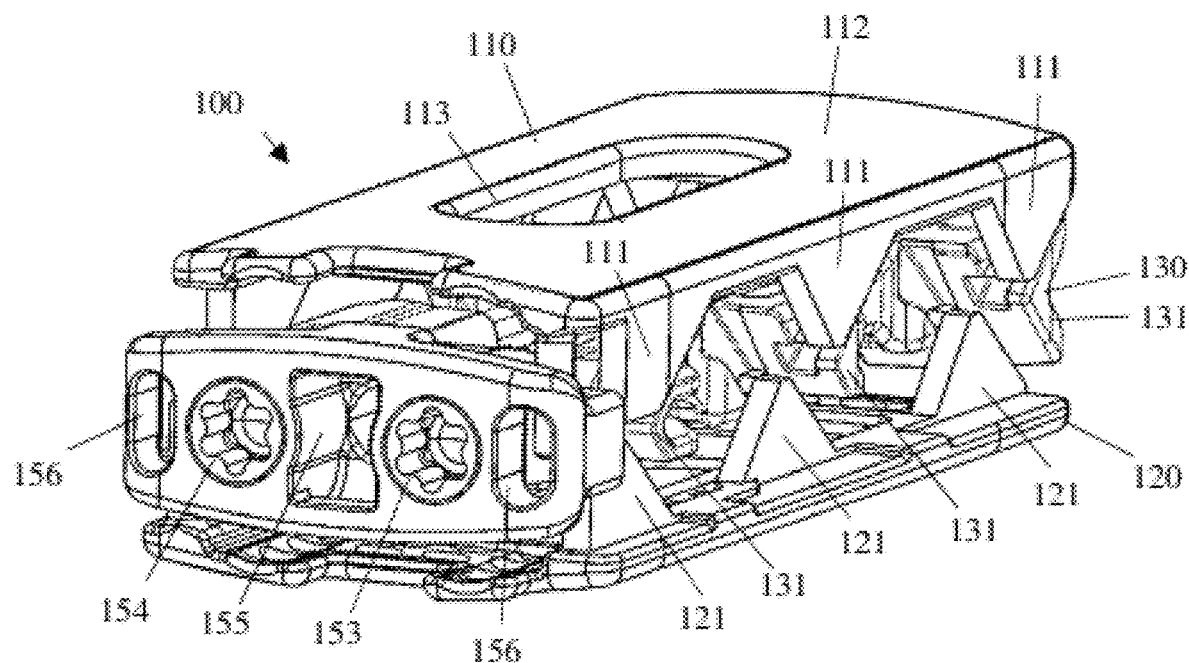
FIG. 4 shows a rear perspective view of the expandable implant in accordance with the first embodiment, in which the expandable implant is expanded in a second configuration.

FIG. 4 shows a rear perspective view of the expandable implant 100 in accordance with the first embodiment, having a first actuator including a first drive screw 153 (FIGS. 6 and 9) and a second actuator including a second drive screw 154 (FIGS. 6 and 9). The actuator housing 150 includes one or more apertures configured to receive at least a portion of the first drive screw 153 and the second drive screw 154 therethrough. The actuator housing 150 is moveably connected to the first endplate 110 and the second endplate 120, allowing movement of the first endplate 110 and the second endplate 110 upon an actuation of the first drive screw 153 and the second drive screw 154.

The actuator housing 150 further includes inserter cavities 156 and a graft aperture 155. The inserter cavities 156 are configured to removably secure the expandable implant 100 to a tip of the inserter. After placing the expandable implant 100 within a prepared intervertebral disc space of a patient, and adjusting the expandable implant 100 to a desired height and angle of lordosis, bone graft or bone graft substitute material may be loaded into an inner volume of the expandable implant 100. In some embodiments the bone graft or bone graft substitute material is delivered to the expandable implant 100 by the inserter and loaded into the inner volume of the expandable implant 100 through the graft aperture 155.

The bone fusion apertures 113, 123 of the first endplate 110 and the second endplate 120 are configured to allow the bone graft or bone graft substitute material packed within the inner volume of the expandable implant to communicate with the vertebral bodies of the patient to assist in the bone fusion process.

The first drive screw 153 and the second drive screw 154 each include a threaded portion 153a, 154a configured to nest within a threaded cavity 132, 142 (FIG. 8) of the first translating member 130 and the second translating member 140 respectively. For example, the threaded portion 153a of the first drive screw 153 is configured to communicate with the threaded cavity 132 of the first translating member 130, and the threaded portion 154a of the second drive screw 154 is configured to communicate with the threaded cavity 142 of the second translating member 140.

At least a portion of the first translating member 130 and the second translating member 140 may be disposed between the first endplate 110 and the second endplate 120. Each of the first translating member 130 and the second translating member 140 may include one or more wedges 131, 141 (FIG. 8) configured to communicate with at least one wedge 111, 121 (FIG. 1-4) of the first endplate 110 and the second endplate 120, upon a movement of the translating member 130, 140. In some embodiments, one or more of the first endplate 110 and the second endplate 120 may include at least one wedge 111, 121 configured to communicate with the one or more wedges 131, 141 of at least one translating member 130, 140.

The first translating member 130 and the second translating member 140 are slideably coupled at the distal end of the expandable implant 100, allowing the first translating member 130 to move independently from the second translating member 140. When the first translating member 130 is simultaneously moved in substantially the same direction and substantially the same distance as the second translating member 140, the one or more wedge 111, 121 of the first endplate 110 and the second endplate 120 will slide up the one or more wedge 131, 141 of the first translating member 130 and the second translating member 140, changing the height of the expandable implant 100. Simultaneous rotation of the first drive screw 153 and the second drive screw 154 is not required to selectively change the height, but the magnitude of distance traveled by the first translating member 130 and the second translating member 140 relative to the drive screws 153, 154 should be substantially equal to minimize an amount of angular actuation of the first endplate 110 relative to the second endplate 120.

Angular actuation of expandable implant 100 may be achieved when one of first translating member 130 and second translating member 140 are moved and when first translating member 130 and second translating member 140 are moved in opposite directions, changing an orientation of first endplate 110 relative to second endplate 120. The change in orientation corresponds to a change in an angle of lordosis of expandable implant 100 (see FIGS. 17 and 21).

As one with skill in the art may appreciate, a patient's condition or other spinal deformity may require an implant of height H. However, the larger the implant, the larger the incision required to place the implant in the intervertebral space of the patient during surgery. Providing an expandable implant 100 allows a surgeon to insert the expandable implant 100 in the first, collapsed configuration, and then expand the expandable implant to the height H with the implant situated in the intervertebral space of the patient, thereby only requiring a minimal incision.

In some embodiments, at least one of first translating member 130 and second translating member 140 may include at least one wedge 131, 141. Each wedge 131, 141 may be configured to communicate with at least one of a wedge 111 of first endplate 110 and at least one wedge 121 of second endplate 120. Upon a movement of first translating member 130 toward actuator housing 150, the at least one wedge 131 of first translating member 130 is configured to communicate with at least one of first endplate 110 and second endplate 120. Similarly, upon of movement of second translating member 140 toward actuator housing 150, the at least one wedge 141 of second translating member 140 is configured to communicate with at least one of first endplate 110 and second endplate 120.

In this embodiment, substantially equal and simultaneous movement of the first translating member 130 and the second translating member 140 in the same direction will change the height and slightly vary the length of the expandable implant 100. The first translating member 130 and the second translating member 140 of this embodiment each include three wedges 131, 141 configured to communicate with opposing wedges 111, 121 of the first endplate 110 and the second endplate 120 upon a movement of the first translating member 130 and the second translating member 140 toward the actuator housing 150.

As one with skill in the art may appreciate, one or more of simultaneous movement of the first translating member 130 and the second translating member 140 in opposite directions, and movement of only one of the first translating member 130 and the second translating member 140, may change the height of each respective end of the expandable implant 100, thereby effectively changing the angle of the first endplate 110 relative to the second endplate 120. In some embodiments, the adjusted angle between the first endplate 110 and the second endplate 120 may include an angle of lordosis.

Figure 5:
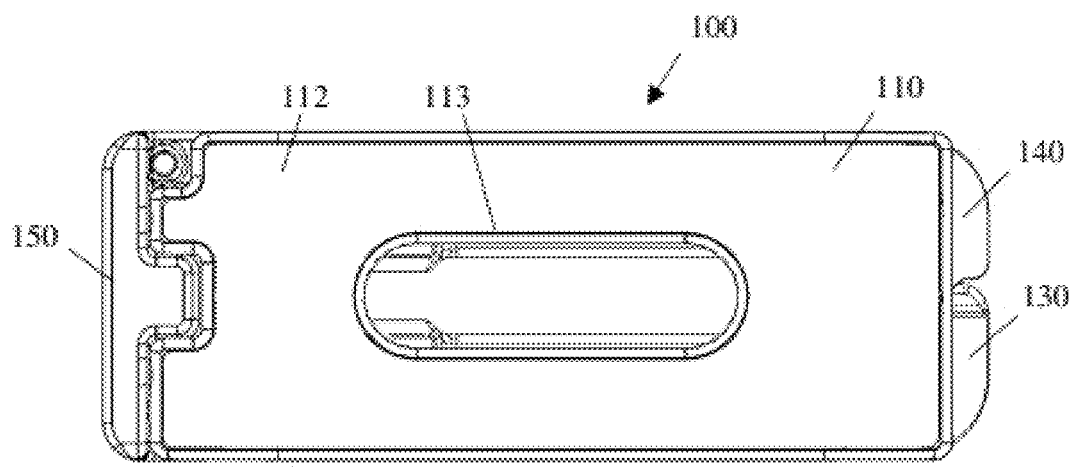
FIG. 5 shows a top view of the expandable implant in accordance with the first embodiment.

FIG. 5 shows a top view of the expandable implant 100 in accordance with the first embodiment. The first endplate 110 and the second endplate 120 shown including a fusion aperture 113, 123 (FIG. 6). The fusion aperture 113 is configured to assist in the bone fusion process, allowing bone graft or bone graft material deposited within an inner volume of the expandable implant, to communicate with the vertebral bodies of the patient. Offsetting the first translating member 130 and the second translating member 140 such that they extend along opposite ends, e.g., first and second ends of the expandable implant creates a cavity within an inner volume of the expandable implant 100. That cavity may be filled with bone graft or bone graft substitute material to aid in the fusion process.

FIG. 6 shows a cross-sectional top view of the expandable implant 100 taken across the plane A (see FIG. 2). Here, a threaded portion 153b of the first drive screw 153 and a threaded portion 154b of the second drive screw 154 are shown, nested within a threaded cavity of the first translating member 130 and a threaded cavity of the second translating member 140 respectively. In this embodiment, the first drive screw 153 and the second drive screw 154 are rotatably captured within the actuator housing 150. This arrangement allows rotational movement of the first drive screw 153 and the second drive screw 154 but prevents translational movement of the first drive screw 153 and the second drive screw 154.

FIG. 7 shows a top view of an expansion mechanism of the expandable implant 100 in accordance with the first embodiment. The expansion mechanism includes the actuator housing 150, the first drive screw 153, the first translating member 130, the second drive screw 154, and the second translating member 140.

As will be described in more detail below, this embodiment also includes an anti-rotation mechanism configured to restrict undesired rotation of the drive screws. In this embodiment the anti-rotation mechanism includes a plurality of flexible members 157, at least a portion of the plurality of flexible members 157 being configured to nest within a plurality of divots of the first drive screw 153 and the second drive screw 154.

Figure 8:
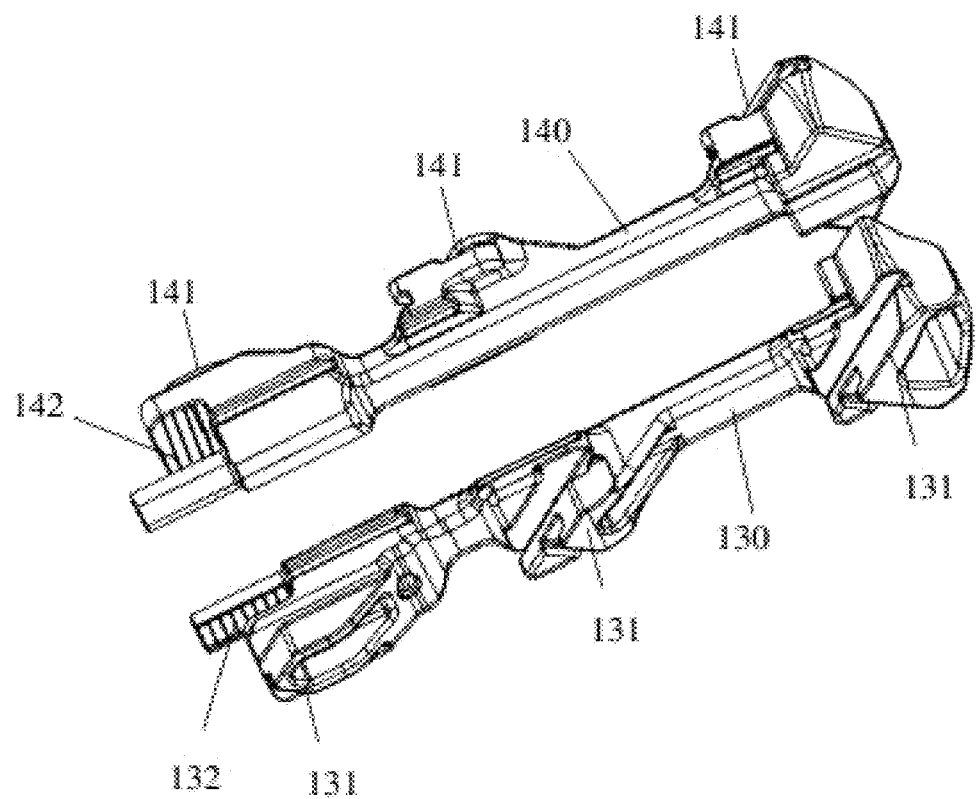
FIG. 8 shows a perspective view of a first translating member and a second translating member of an expandable implant in accordance with the first embodiment.

FIG. 8 shows a perspective view of a first translating member 130 and a second translating member 140 of an expandable implant 100. First translating member 130 and second translating member 140 include a threaded aperture 132, 142 configured to communicate with threaded portion 153a, 154a of a drive screw 153, 154. Translating members 130, 140 each further include a plurality of wedges 131, 141 configured to communicate with wedges 111, 121 of first endplate 110 and second endplate 120 and configured to move first endplate 110 relative to second endplate 120.

FIG. 9 shows a perspective view of an actuator housing 150 of an expandable implant 100 having a first drive screw 153 and a second drive screw 154 nested therein. The actuator housing 150 shown includes a plurality of flexible members 157 configured to restrict undesired movement of the first drive screw 153 and the second drive screw 154.

Figure 10:
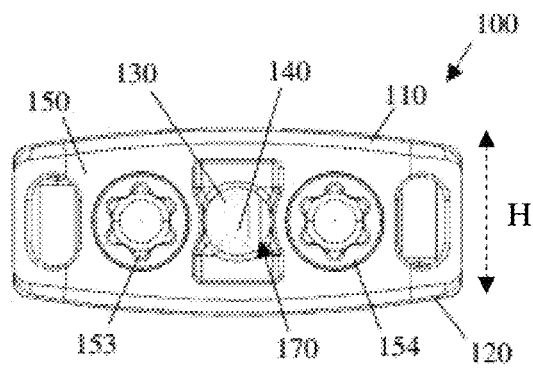
FIG. 10 shows a rear view of the expandable implant in accordance with the first embodiment, which is collapsed in the first configuration.
Figure 11:
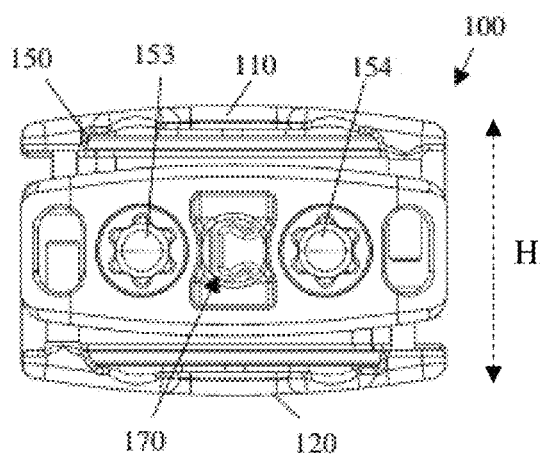
FIG. 11 shows a rear view of the expandable implant in accordance with the first embodiment, which is expanded in the second configuration.

FIGS. 10-15 show two perspective views, front and back, of the expandable implant 100 as it is adjusted from the first, collapsed configuration to the second, expanded configuration. FIG. 10 shows a rear view of the expandable implant 100 collapsed in the first configuration. Note the relative locations of the first endplate 110 and the second endplate 120. FIG. 11 shows a rear view of the expandable implant 100 expanded in the second configuration. Note the movement of the first endplate 110 relative to the second endplate 120, and the change of height of the expandable implant 100.

Figure 12:
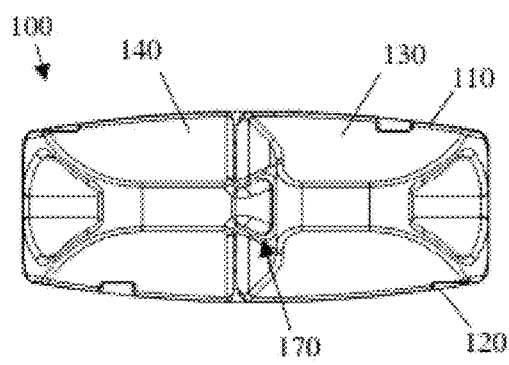
FIG. 12 shows a front view of the expandable implant in accordance with the first embodiment, which is collapsed in the first configuration.
Figure 13:
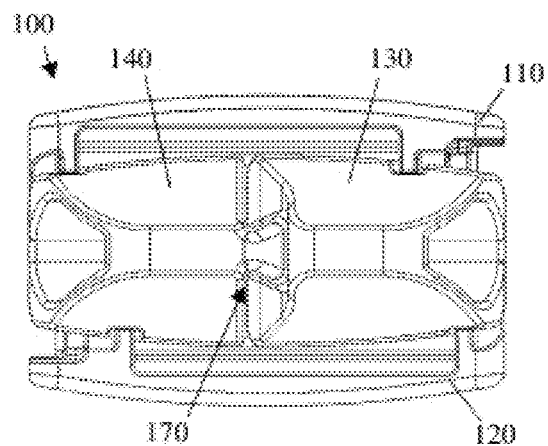
FIG. 13 shows a front view of the expandable implant in accordance with the first embodiment, which is expanded in the second configuration.

As seen from another perspective, FIG. 12 shows a front view of the expandable implant 100 collapsed in the first configuration and FIG. 13 shows a front view of an expandable implant 100 expanded in the second configuration.

To illustrate angular adjustment of the expandable implant 100, FIG. 14 shows a rear view of the expandable implant 100 in accordance with the first embodiment, adjusted to an exemplary angle of lordosis. FIG. 15 shows a front view of expandable implant 100 in accordance with the first embodiment, adjusted to an exemplary angle of lordosis. By comparing this configuration with the first and second configurations described above, we see that first endplate 110 sits at an angle relative to second endplate 120, corresponding to an exemplary angle of lordosis.

FIG. 16 shows a perspective view of the expandable implant 100 in accordance with the first embodiment adjusted to an exemplary angle of lordosis. Depending on the needs of the patient, the individual components of the expandable implant may be sized to provide the required amount of lordosis.

The expandable implant 100 includes a slideable interface 170 (FIGS. 6-7 and 10-16) disposed at the distal end of the expandable implant 100. The distal end of the expandable implant 100, and particularly the distal ends of the first translating member 130 and the second translating member 140, are configured with a tapered edge having a slidable interface 170 moveably coupling the first translating member 130 to the second translating member 140. The tapered edge is configured to aid in insertion of the expandable implant into an intervertebral disc space of the patient, and the slideable interface 170 is configured to increase the stability and loadbearing characteristics of the expandable implant 100.

In this embodiment, the slidable interface 170 includes a dovetail coupling, the dovetail coupling including an extension of the first translating member 130 nested within a channel of the second translating member. As one with skill in the art may appreciate, in this embodiment the extension is a portion of the first translating member 130 and the channel is disposed on the second translating member 140. In some embodiments, the extension is a portion of the second translating member 140 and is in communication with a channel of the first translating member 130. Similarly, in this embodiment the slidable interface 170 is a dovetail coupling, having a substantially triangular geometry, and as one with skill in the art may appreciate other geometries may be provided.

FIGS. 17-20 show a second embodiment of an expandable implant 200 including: a first endplate 210, a second endplate 220, a first translating member 230 disposed between first endplate 210 and second endplate 220 and moveably coupled to a first drive screw 253, and a second translating member 240 disposed between the first endplate 210 and second endplate 220 and moveably coupled to a second drive screw 254. First translating member 230 is configured to move independently from second translating member 240, and first translating member 230 and second translating member 240 are configured to change a spatial relationship between first endplate 210 and second endplate 220. First and second translating members 230, 240 are mirror images of each other, and therefore, have corresponding features.

In this embodiment, the first endplate 210 and the second endplate 220 include a porous bone contact surface 211, 221. The first endplate 210, the second endplate 220, and any other component of the expandable implant 200 may be fabricated using additive manufacturing techniques. The porous bone contact surface 211, 221 may be printed using an additive manufacturing technique. In some embodiments, the first endplate 210, the second endplate 220, and any other component of the expandable implant 200 may comprise polyether ketone (PEEK). As such, the porous bone contact 211, 221 surface may be fabricated using any known process for manufacturing porous PEEK implants. In some embodiments, the expandable implant 200 may be manufactured from titanium, and any other material commonly used in fabrication of medical implants.

Figure 17:
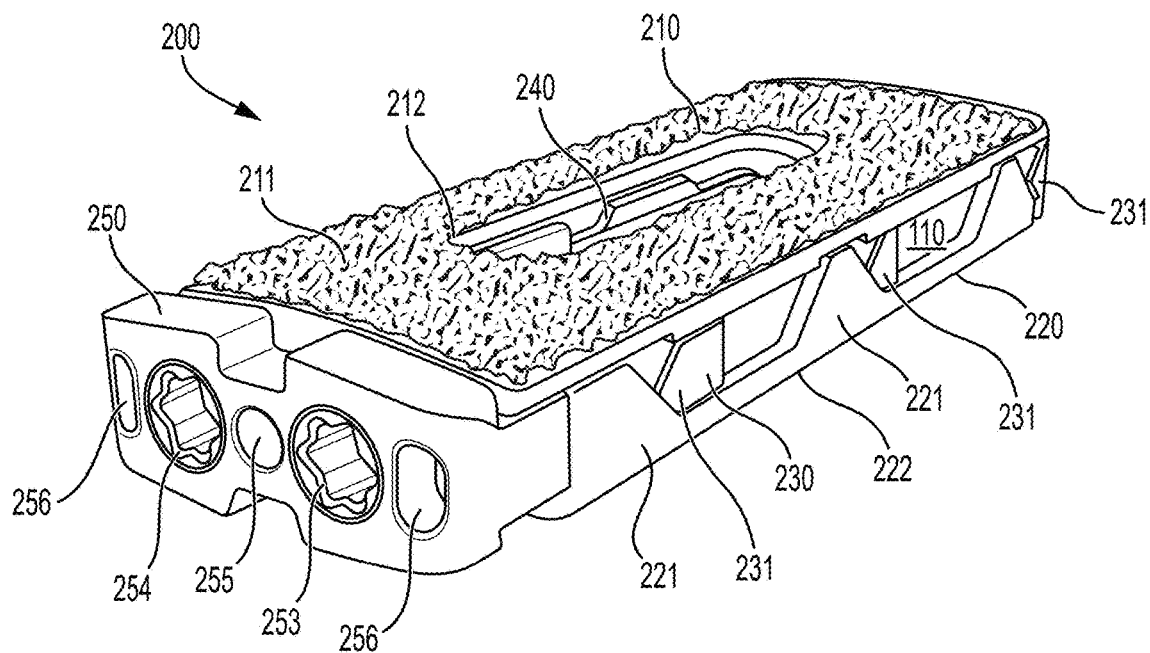
FIG. 17 shows a rear perspective view of an expandable implant in accordance with a second embodiment, which is collapsed in a first configuration.

FIG. 17 shows the expandable implant 200 in a first collapsed configuration. The expandable implant 200 includes: a first endplate 210, a second endplate 220, a first translating member 230, a second translating member 240, and an actuator housing 250. The actuator housing 250 includes a first drive screw 253 with a first threaded portion in communication with a threaded cavity of the first translating member 230, and a second drive screw 254 in communication with a first threaded cavity of the second translating member 240.

Upon a rotation of at least one of the first drive screw 253 and the second drive screw 254, communication of the threaded portion (not shown in FIG. 17, but similar to 153a, 154a (FIG. 6) relative to implant 100) with the first threaded cavity 232, 242 of the first translating member 230 and the second translating member 240, thereby translating the first translating member 230 and/or the second translating member 240.

Each of the first translating member 230 and the second translating member 240 may include at least one wedge 231, 241, with each wedge 231, 241 configured to communicate with a wedge 211, 221 of the first endplate 210 and the second endplate 220. Upon a translation of one or more of the first translating member 230 and the second translating member 240, the one or more wedges 231, 241 of the translating members 230, 240 are configured to communicate with one or more wedges 211, 221 of the endplates 210, 220 and thereby change a dimension of the expandable implant 200. While not shown in FIGS. 17-18, it is to be understood that second translating member 240 includes wedges 241 since translating member 240 is a mirror image of translating member 230.

In this embodiment, the wedges 211, 221 of the endplates 210, 220 include a keyed portion configured to travel in a track of the wedges 231, 241 of the translating members 230, 240. The keyed portion traveling in the track is configured to provide additional stability and load support characteristics to the expandable implant.

Figure 18:
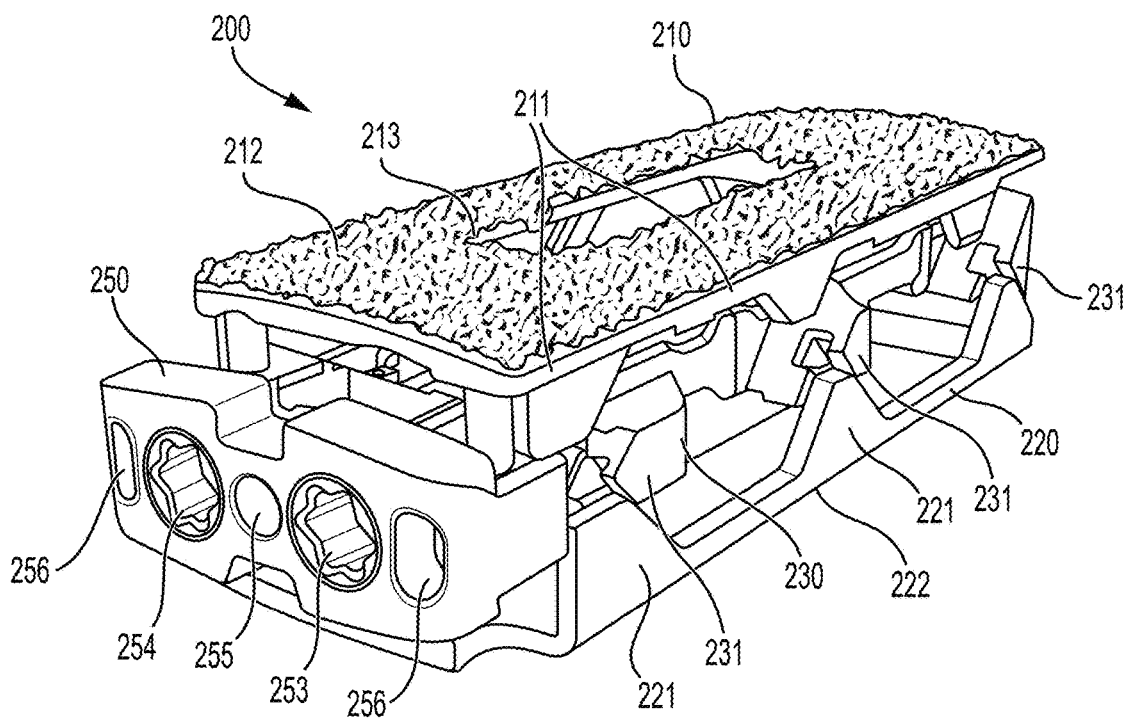
FIG. 18 shows a rear perspective view of an expandable implant in accordance with a second embodiment, which is expanded in a second configuration.

FIG. 18 shows a rear perspective view of the expandable implant 200 in its second, expanded configuration. When the first drive screw 253 and the second drive screw 254 are rotated such the first translating member 230 and the second translating member 240 move a substantially equal amount, the wedges 231, 241 of the first translating member 230 and the second translating member 240 communicate with the wedges 211, 221 of the first endplate 210 and the second endplate 220, to displace the first endplate 210 and second endplate 220 relative to the actuator housing 250. In this embodiment, this movement will expand the expandable implant 200, changing the height of the expandable implant 200.

Figure 19:
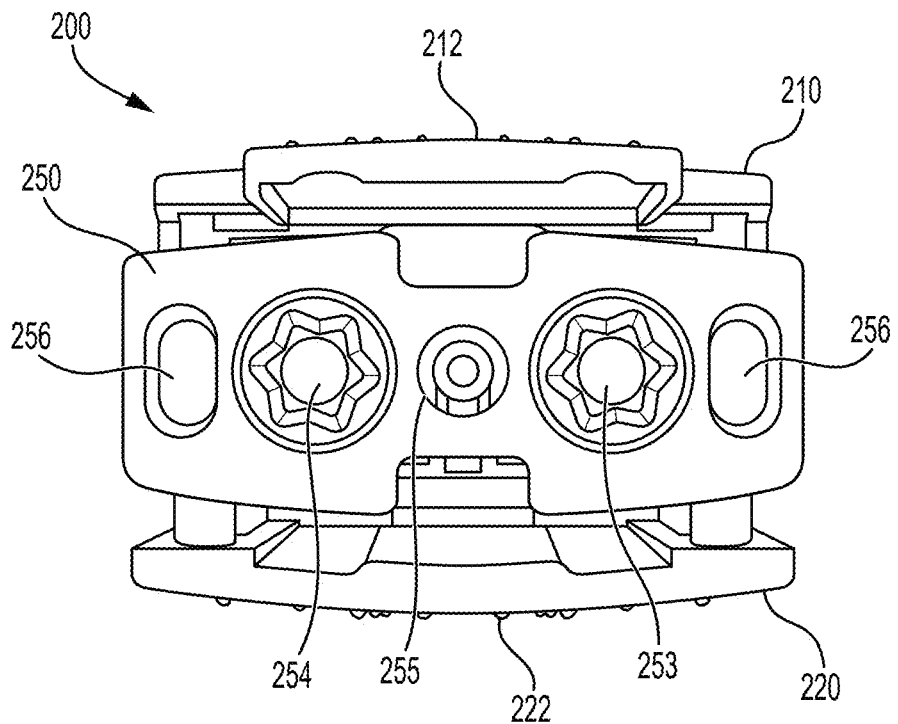
FIG. 19 shows a rear view of the expandable implant in accordance with the second embodiment, which is expanded in the second configuration.

Now, in some embodiments the expandable implant 200 is also configured to be adjusted for an angle of lordosis. For reference, FIG. 19 shows a rear view of the expandable implant 200 in the same second, expanded configuration of FIG. 18. As one with skill in the art may appreciate, by either rotating one of the first drive screw 253 and the second drive screw 254, and by rotating both the first drive screw 253 and the second drive screw 254 in opposite directions, will change an angle between the first endplate 210 and the second endplate 220.

Figure 20:
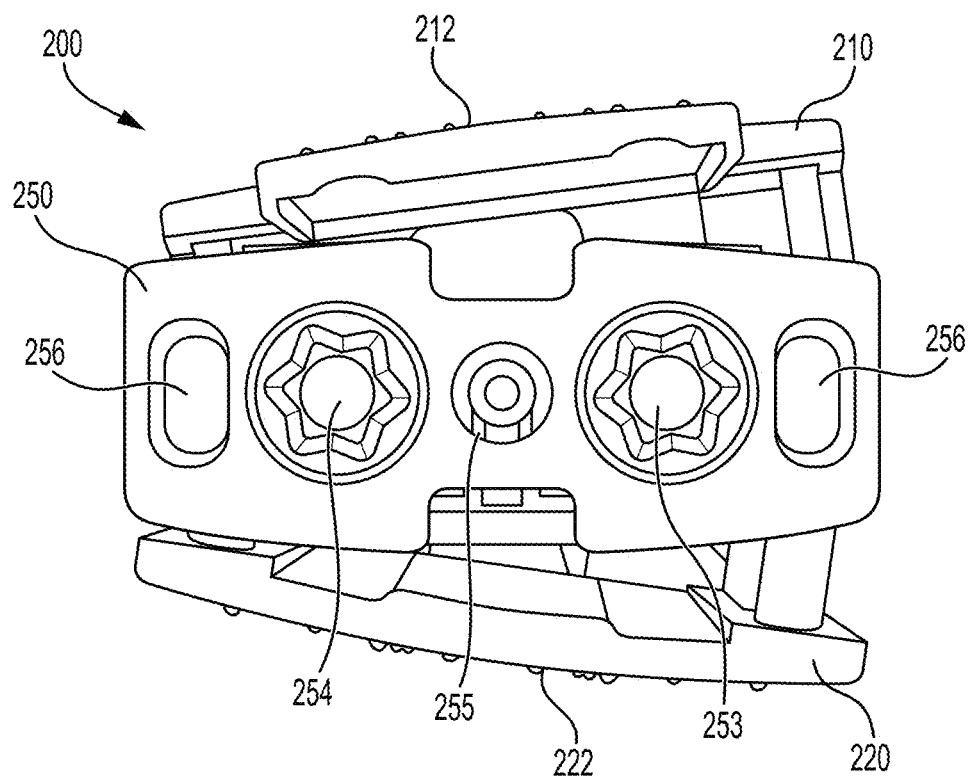
FIG. 20 shows a rear view of the expandable implant in accordance with the second embodiment adjusted to the third configuration having an angle of lordosis.

FIG. 20 shows a rear view of the expandable implant 200 adjusted to a third configuration having a chosen angle of lordosis. As one with skill in the art may appreciate, choosing the dimensions of the wedges 211, 221 of the endplates 210, 220, and the wedges 231, 241 of the translating members 230, 240 will determine a range of angles of lordosis the expandable implant 200 is configured to provide.

As one with skill in the art may appreciate, the first embodiment 100, the second embodiment 200, and all embodiments shown and described herein may be adjusted in both height and angle of lordosis. Any number of configurations of height and lordosis may be provided by the expandable implant, but may not be shown explicitly herein. In this sense, the full range of possible adjustments should be viewed as being encompassed by this disclosure, and the disclosure is not to be limited by the configurations explicitly shown herein.

Figure 21:
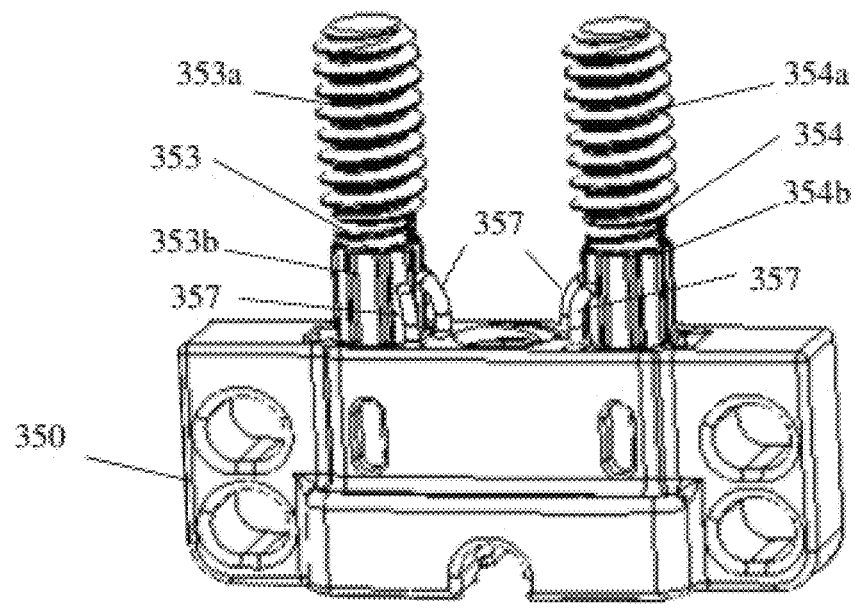
FIG. 21 shows an actuator housing of an expandable implant in accordance with a third embodiment having an anti-rotation feature configured to restrict a rotation of the drive screws.
Figure 22:
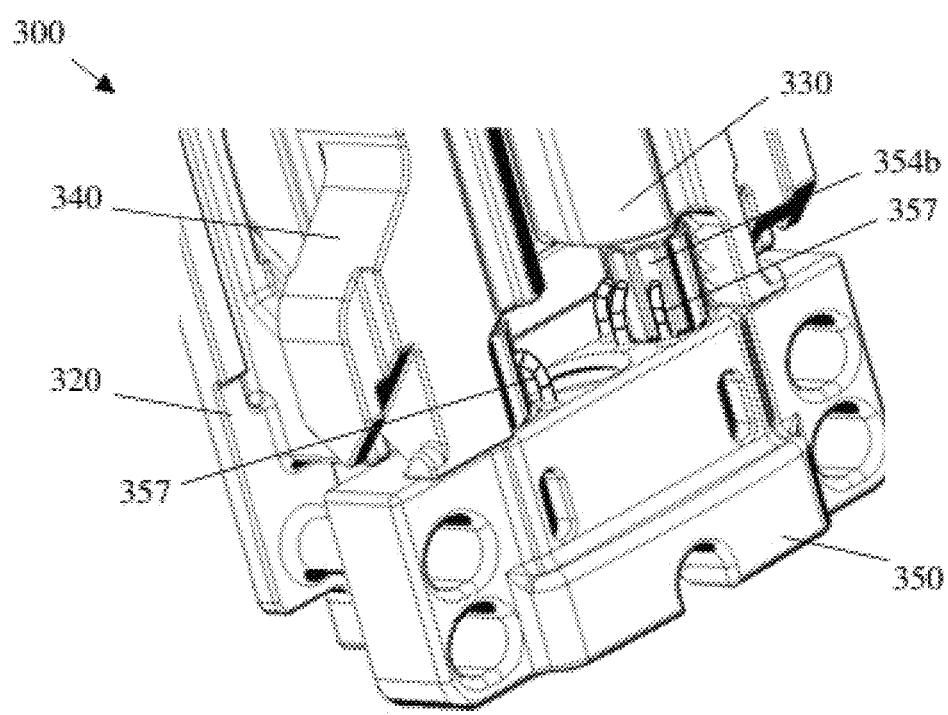
FIG. 22 shows a perspective view of an expandable implant in accordance with the third embodiment.

Some embodiments may include anti-rotation features to restrict undesired rotation of the lead screws. The anti-rotation features provide added rigidity and increase an amount of load the expandable implant is capable of supporting. For example, FIG. 21 and FIG. 22 show an actuator housing 350 of an expandable implant 300 in accordance with a third embodiment, the actuator housing 350 including an anti-rotation feature 357 configured to restrict an undesired rotation of the first drive screw 353 and the second drive screw 354. In this embodiment, the anti-rotation features 357 include a plurality of flexible members 357 extending from the actuator housing 350. The first drive screw 353 and the second drive screw 354 of this embodiment include a plurality of divots 353b, 354b, each configured to receive at least a portion of each of the plurality of flexible members 357 therein with the anti-rotation feature configured to ratchet and prevent undesired rotation of the drive screws 353, 354.

As one with skill in the art may appreciate, communication of at least a portion of each of the plurality of flexible members 357 nesting within the plurality of divots 353b, 354b increases the force requirement needed to rotate the drive screws 353, 354. However, the ratchet mechanism of the plurality of flexible members 357 communicating with the divots 353b, 354b of the drive screws 353, 354, acts to prevent undesired rotation of the drive screws 353, 354, and helps prevent collapse of an expandable implant 300.

In some embodiments, the actuator housing 350 may be fabricated using additive manufacturing techniques, and the plurality of flexible members 357 may be fabricated such that the actuator housing 350 and the plurality of flexible members 357 form a monolithic piece. In some embodiments, this single monolithic piece may be 3D printed directly around the drive screws, to reduce the number of components and aid in the assembly process. In some embodiments, the drive screws are inserted through respective cavities and seated into place with a friction fit.

Figure 23:
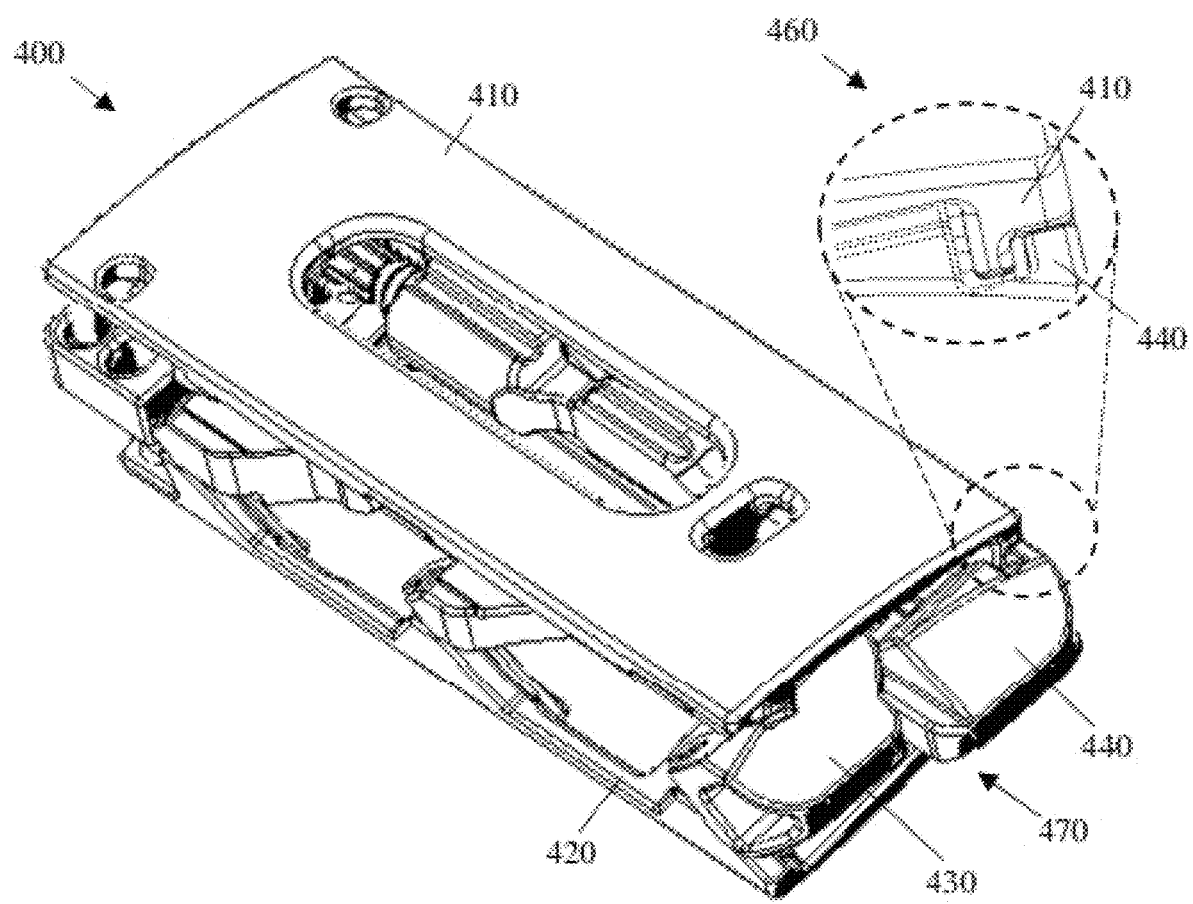
FIG. 23 shows an expandable implant in accordance with a fourth embodiment, the expandable implant having a sliding interface.

FIG. 23 shows an expandable implant 400 in accordance with a fourth embodiment, adjusted to a chosen height and angle of lordosis. The expandable implant 400 includes a sliding interface 460 formed at the interface of the ends of the endplates 410, 420 and each of the translating members 430, 440. An enhanced view of the sliding interface 460 of the first endplate 410 and the second translating member 440. This sliding interface 460 between the endplates 410, 420 and the translating members 430, 440 helps the expandable implant 400 achieve an increased amount of lordosis.

In this embodiment, sliding interfaces 460 are formed by providing at least one groove along the length of the translating members 430, 440 and a plurality of notches extending along at least a portion of the length of endplates 410, 420. As the expandable implant is adjusted to particular angle of lordosis, the pivot point of the first endplate 410 and the second endplate 420 will change. As the pivot point moves toward an end of the endplate 410, 420, the translating member 430, 440 may abut and effectively restrict movement of the endplate 410, 420. However, by providing a sliding interface 460, the endplate is provided an increased amount of travel.

Figure 24:
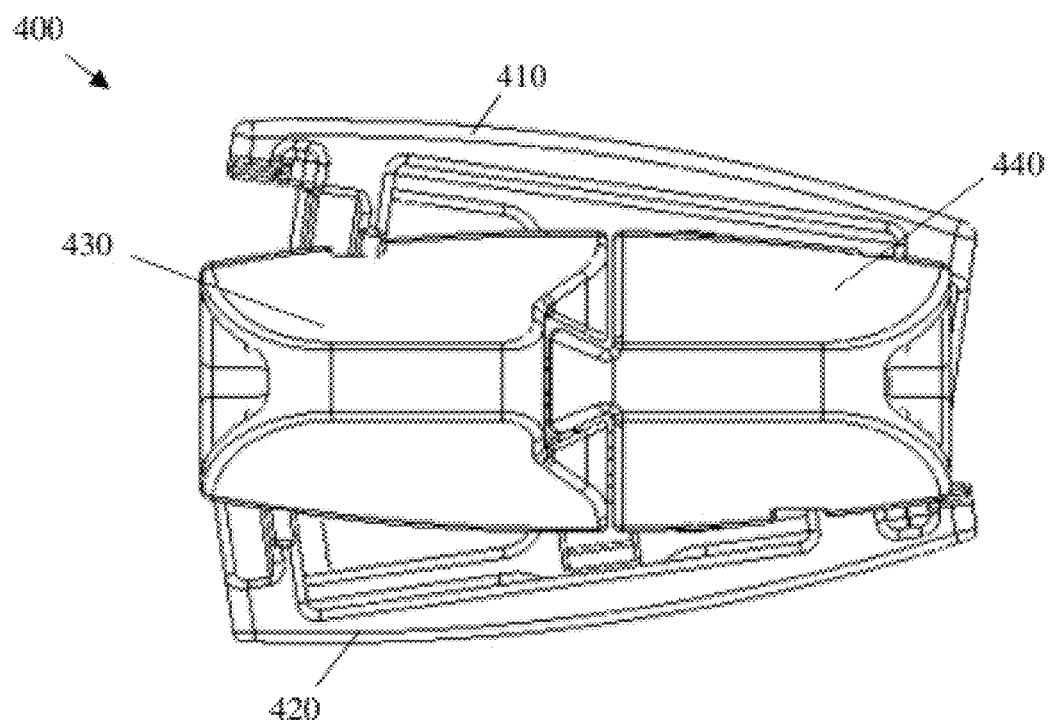
FIG. 24 shows the expandable implant in accordance with the fourth embodiment adjusted to an angle of lordosis.

In some embodiments, the first translating member 430 and the second translating member 440 may be moveably coupled at the distal end of the expandable implant by slideable interface 470. The slideable interface 470 may be configured to allow the first translating member 430 and the second translating member 440 to move independently. FIG. 24 shows the distal end of the expandable implant 400, the slideable interface 470 (FIG. 25) having a dovetail coupling that slideably connects the first translating member 430 and the second translating member 440. The dovetail coupling is configured to allow the first translating member 430 and the second translating member 440 to move independently. Similarly, in some embodiments the first translating member 430 and the second translating member 440 may be moveably coupled at the proximal end of the expandable implant by a slideable interface configured to allow the first translating member 430 and the second translating member 440 to move independently.

Figure 25:
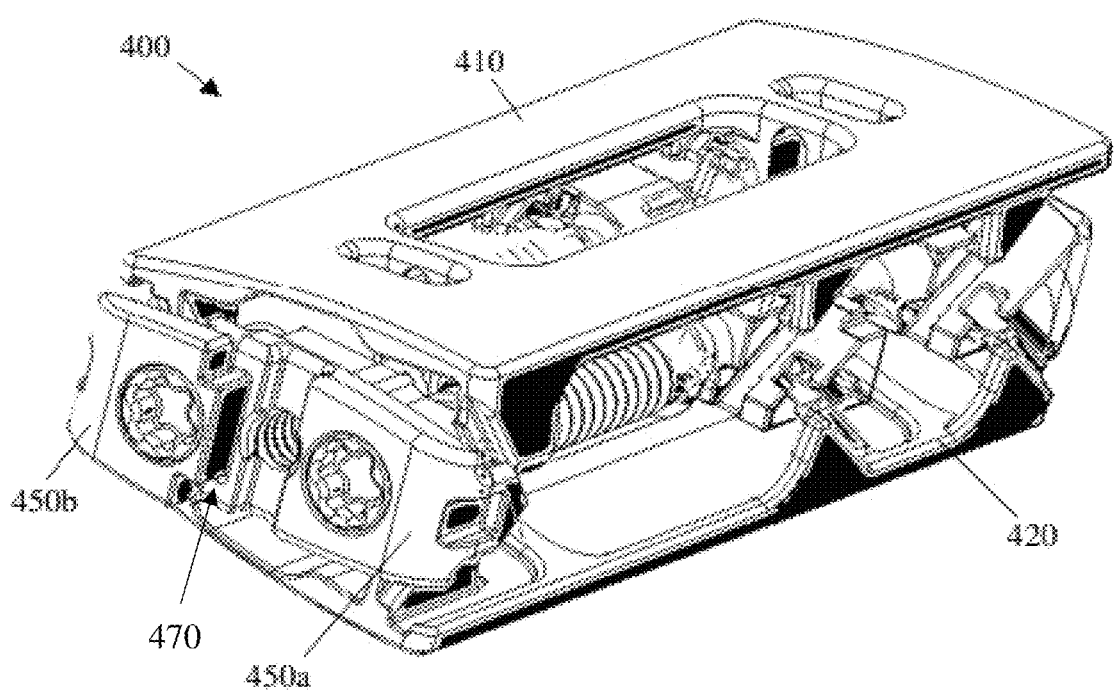
FIG. 25 shows an expandable implant in accordance with a fourth embodiment, the actuator housing including a dove tail coupling configured to move independently.
Figure 26:
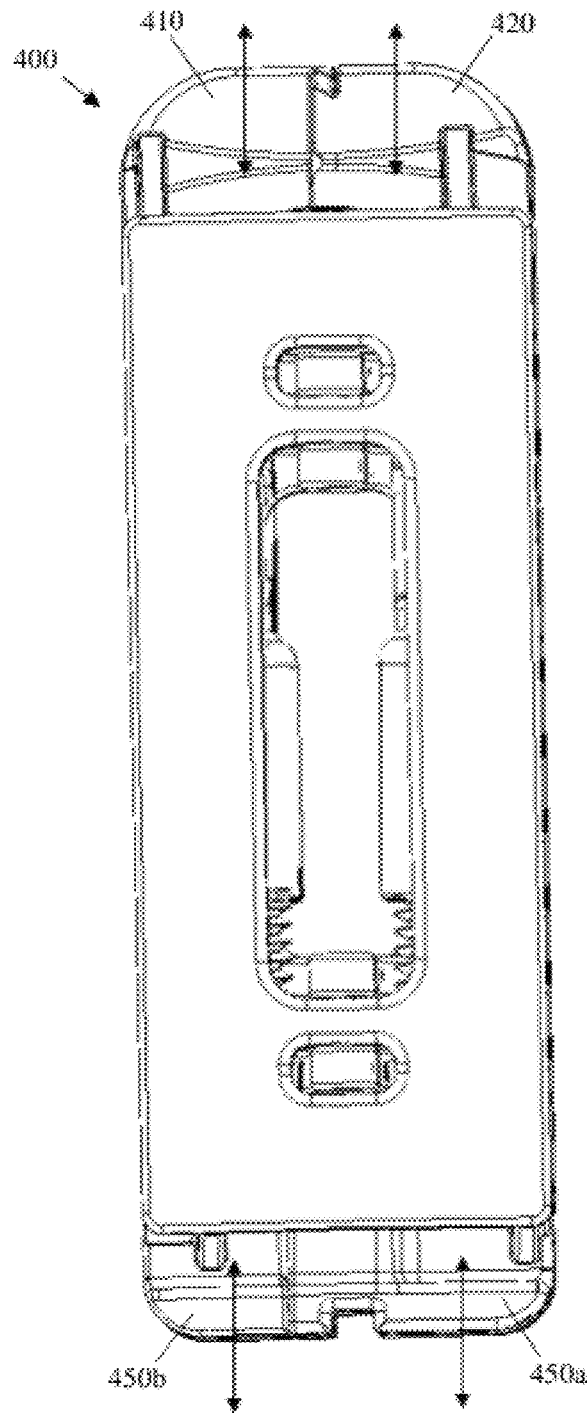
FIG. 26 shows a top view of the expandable implant in accordance with the fourth embodiment.
Figure 27:
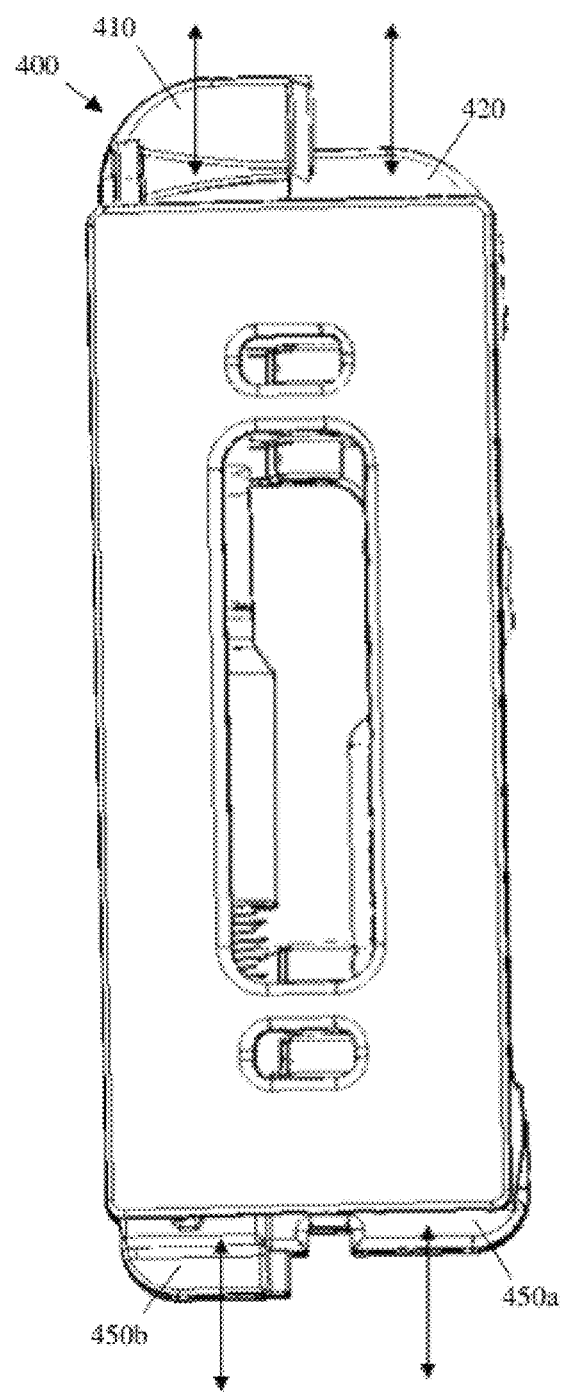
FIG. 27 shows a top view of the expandable implant in accordance with the fourth embodiment in an adjusted configuration.

In some embodiments, a slideable interface 470 at a proximal end of the expandable implant 400 maybe formed between a first actuator housing 450a and a second actuator housing 450b (FIGS. 25-27). FIG. 25 shows a proximal end of the expandable implant 400 having a slideable interface 470 configured to provide a moveable coupling between a first actuator housing 450a and a second actuator housing 450b. The slideable interface 470 includes a dovetail coupling configured to allow the first actuator housing 450a and the second first actuator housing 450b to move independently.

Providing a slideable coupling at both the proximal and distal ends of the expandable implant provides additional stability and load bearing characteristics to the expandable implant. Additionally, providing a slideable coupling at both the proximal and distal ends of the expandable implant may allow length expansion and length contraction of the expandable implant at either end of the expandable implant. For example, FIGS. 26-27 show top views of the expandable implant 400 in accordance with the fourth embodiment. In FIG. 26, the expandable implant 400 is arranged in a first collapsed configuration. In FIG. 27, the first drive screw has been rotated, to adjust an angle of lordosis of the expandable implant 400. As such, the first actuator housing 450*a* has moved toward the first translating member 430, pivoting the first endplate 410 and the second endplate 420.

Figure 28:
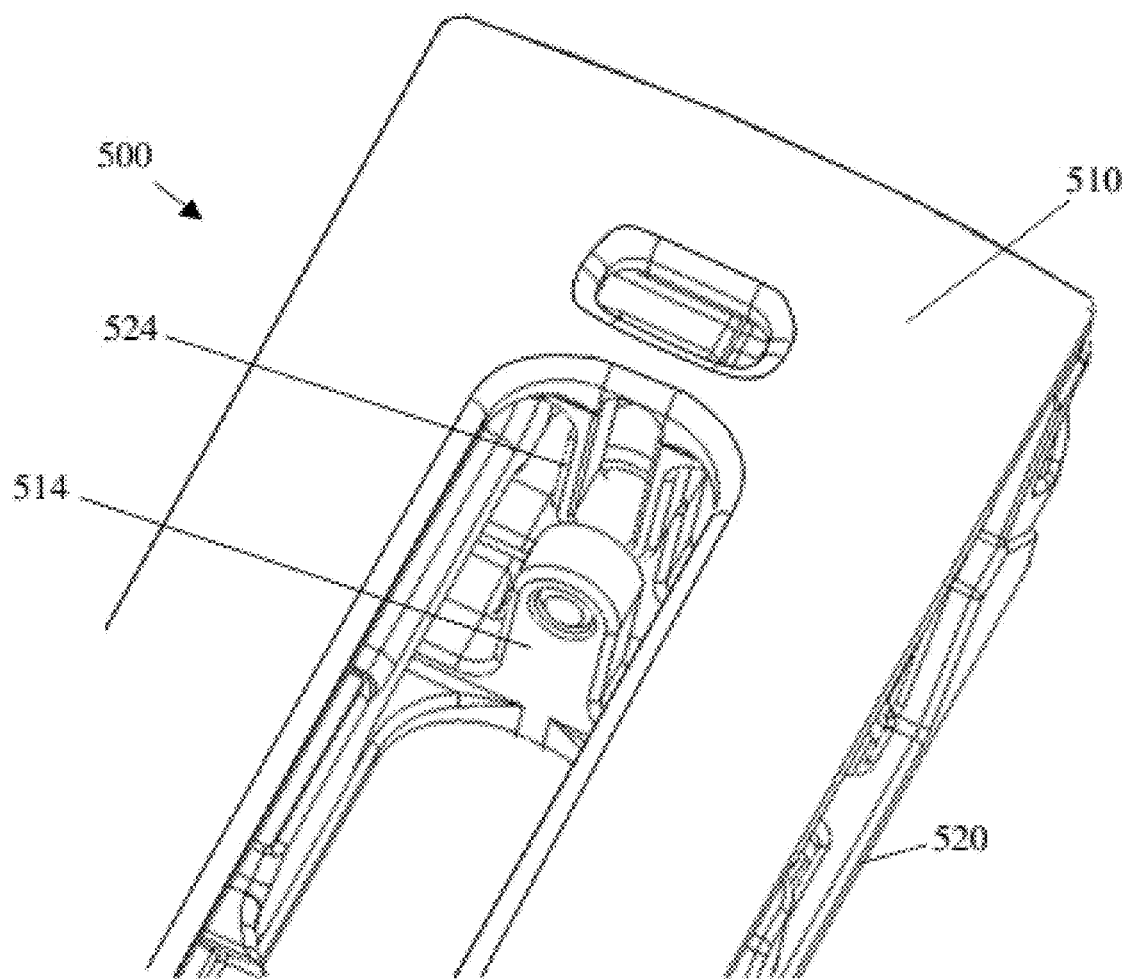
FIG. 28 shows a top view of an expandable implant in accordance with the fifth embodiment including a hinge joint.

With reference to FIG. 28, in some embodiments, one or more hinge joints may be provided. The hinge joint may be configured to provide additional stability to the expandable implant. The hinge joint may moveably couple the first endplate 510 to the second endplate 520. In some embodiments, the first endplate 510 and the second endplate 520 may be coupled at the posterior end or the anterior end. In some embodiments, the first endplate 510 and the second endplate 520 may be moveably coupled by linkages. For example, FIG. 28 shows an expandable implant 500 in accordance with a fifth embodiment, the first endplate 510 having a linkage 514 moveably coupled to a linkage 524 of the second endplate 520. The linkage 514 of the first endplate 510 is moveably coupled to the linkage 524 of the second endplate 520 by a coupling pin. These linkages 514, 524 moveably couple the first endplate 510 to the second endplate 520 and improve stability and load bearing characteristics of the expandable implant 500.

A method is further provided for treating a spinal condition using an expandable implant. The method may include accessing an intervertebral disc space via a generally lateral approach, and inserting an expandable implant into the intervertebral disc space, the expandable implant having a first translating member moveably coupled to a first actuator and a second translating member moveably coupled to a second actuator. The first translating member and the second translating member may be configured to change a spatial relationship between the first endplate and the second endplate as they move. The method may further include actuating at least one of the first actuator and the second actuator to change the spatial relationship between the first endplate and the second endplate to change a dimension of the expandable implant.

In some embodiments, the method may include the step of adjusting the expandable implant in situ within the intervertebral disc space of the patient.

In some embodiments, the method may include the step of packing the expandable implant with bone graft or bone graft substitute material. This step may occur prior to inserting the implant into the disc space or after placing the implant in the disc space by using a specialized inserter to provide the bone graft or bone graft substitute material to the expandable implant in situ.

Figure 29:
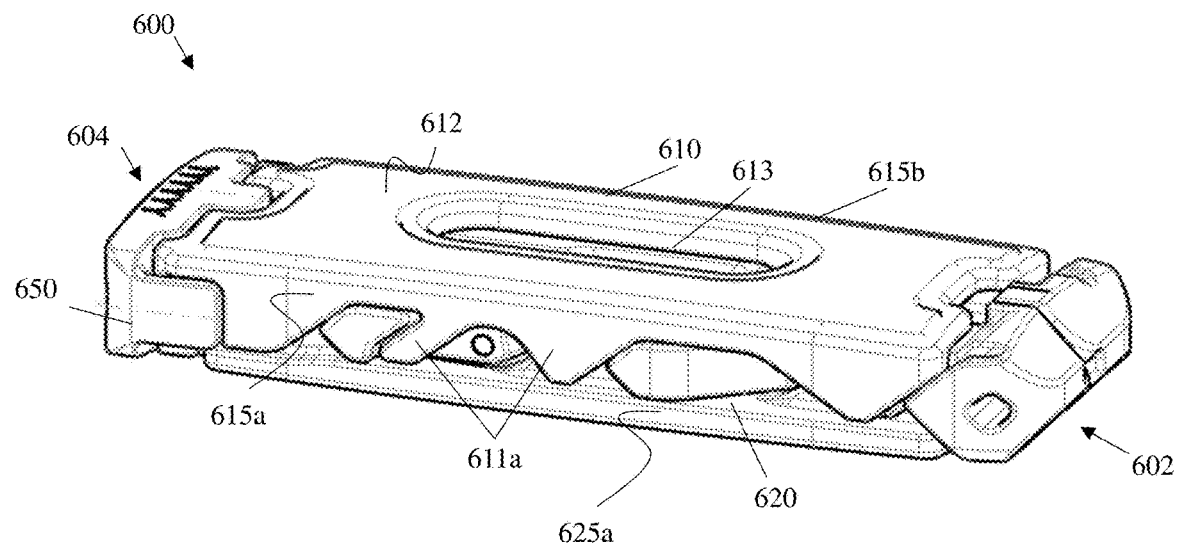
FIG. 29 shows a front perspective view of the expandable implant in accordance with a fifth embodiment, the expandable implant being in a collapsed configuration.
Figure 30:
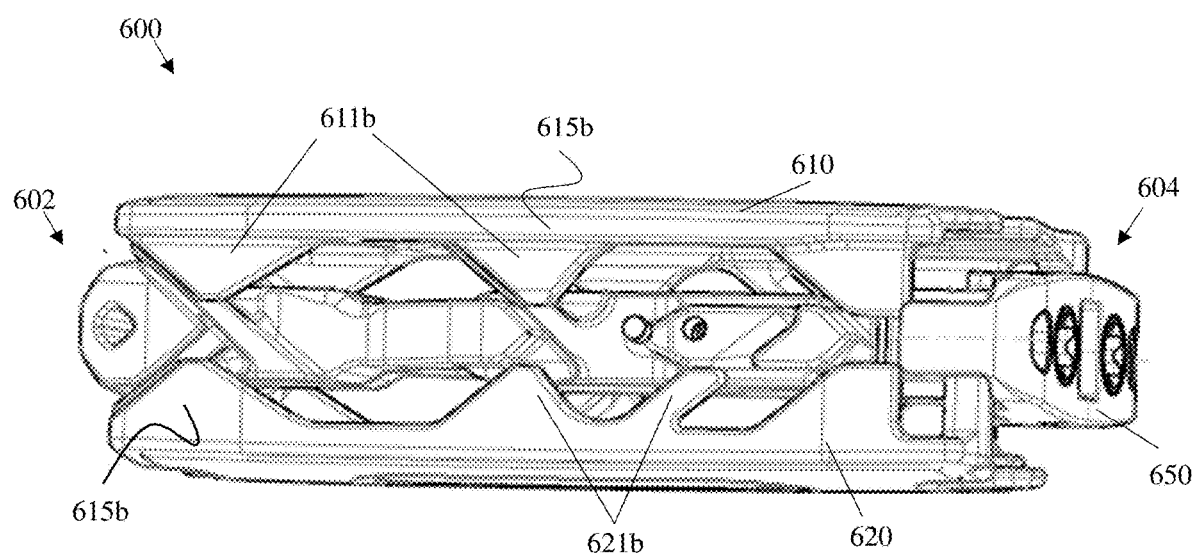
FIG. 30 shows a side perspective view of the expandable implant in accordance with the fifth embodiment, the expandable implant being in an expanded configuration.

In some embodiments, the method may include the step of adjusting the expandable implant to a desired height, and may additionally or alternatively include the step of adjusting the expandable implant to a desired angle of lordosis. FIG. 29 illustrates an expandable fusion intervertebral implant device 600 according to another embodiment. As shown in FIG. 29, the expandable fusion intervertebral device 600 is in a collapsed, insertion configuration. FIG. 30 illustrates the expandable fusion intervertebral implant device of FIG. 29 in its fully expanded configuration 600. According to this exemplary embodiment, the expandable fusion device 600 is configured to have a first side and a second side that are independently expandable, such that a user may choose to expand (i.e., increase the height/distance between the first endplate 610 and the second endplate 620) only the first side of the implant or the second side of the implant. Expanding only the first side or second side of the implant will result in a so-called lordotic implant. In other words, the height of the expanded side is greater than the height of the unexpanded side, creating an angle (i.e., lordosis or a lordotic angle) between the first endplate 610 and the second endplate 620.

According to the exemplary embodiment shown in FIGS. 29-35, the expandable fusion intervertebral implant device 600 is dimensioned to span the width of a vertebral endplate, from the ipsilateral aspect of a vertebral body to the contralateral aspect of the vertebral body. By way of example, an expandable fusion intervertebral implant device 600 may range from about 40 mm to about 60 mm in length from leading end 602 to trailing end 604. The expandable fusion intervertebral implant device 600 is dimensioned to be placed in the intervertebral space from a lateral approach, e.g., direct lateral/transpsoas approach or anterolateral/anterior to psoas approach. By way of example, the width of the expandable fusion intervertebral implant device 600 may range from about 18 mm to about 28 mm from the first side to the second side of the expandable fusion intervertebral implant device 600. It is also contemplated that the expandable fusion intervertebral implant device 600 in its collapsed configuration has parallel or substantially parallel endplates, i.e., approximately 0° of lordosis. It is also contemplated that the expandable fusion intervertebral implant device 600 in its collapsed state has a lordotic angle between the endplates 610, 620. By way of example, the angle between the first endplate 610 and the second endplate 620 in a collapsed configuration may range from 0° to 15°.

Figure 31:
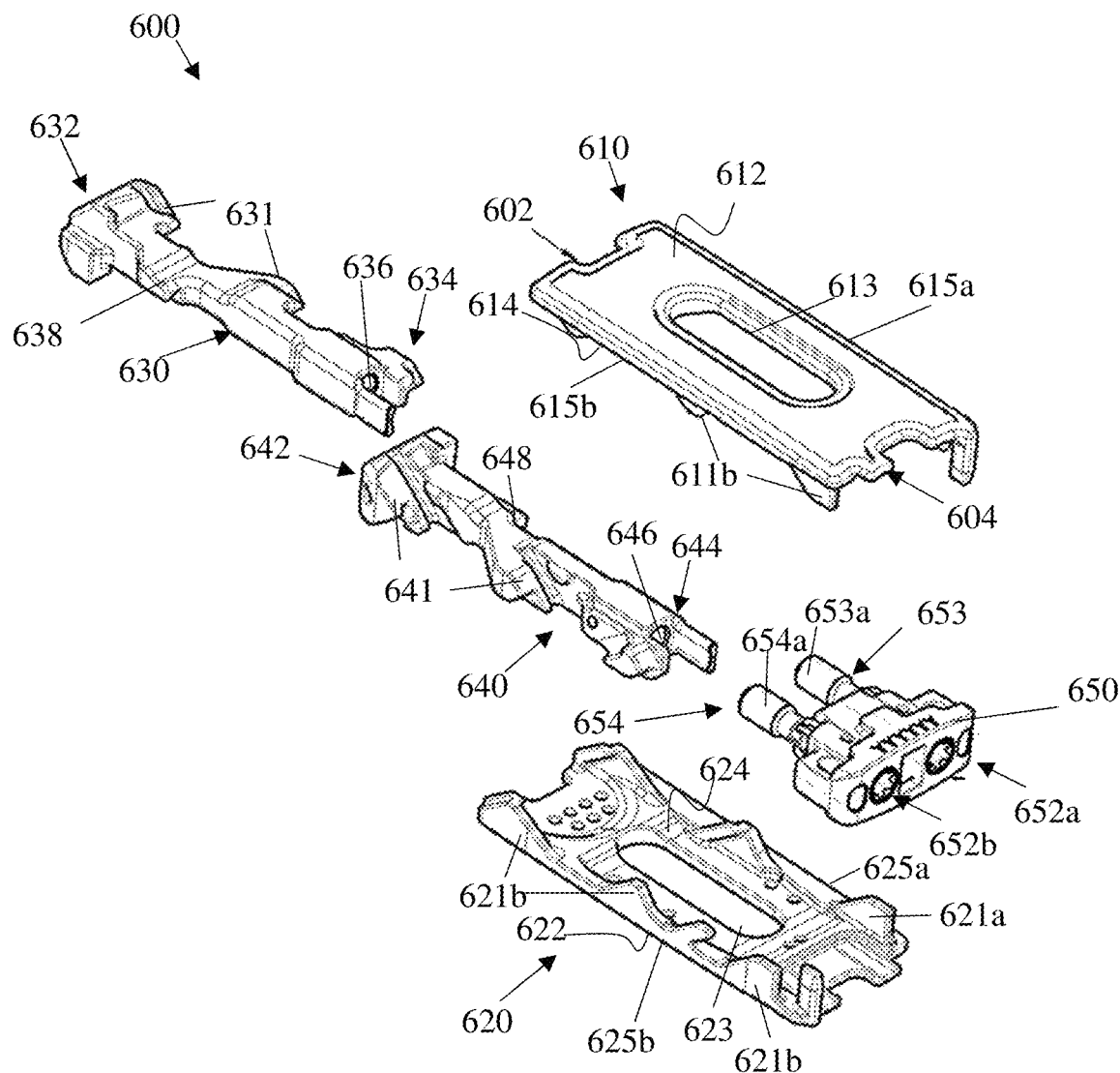
FIG. 31 shows an exploded view of the expandable implant in accordance with the fifth embodiment.
Figure 32:
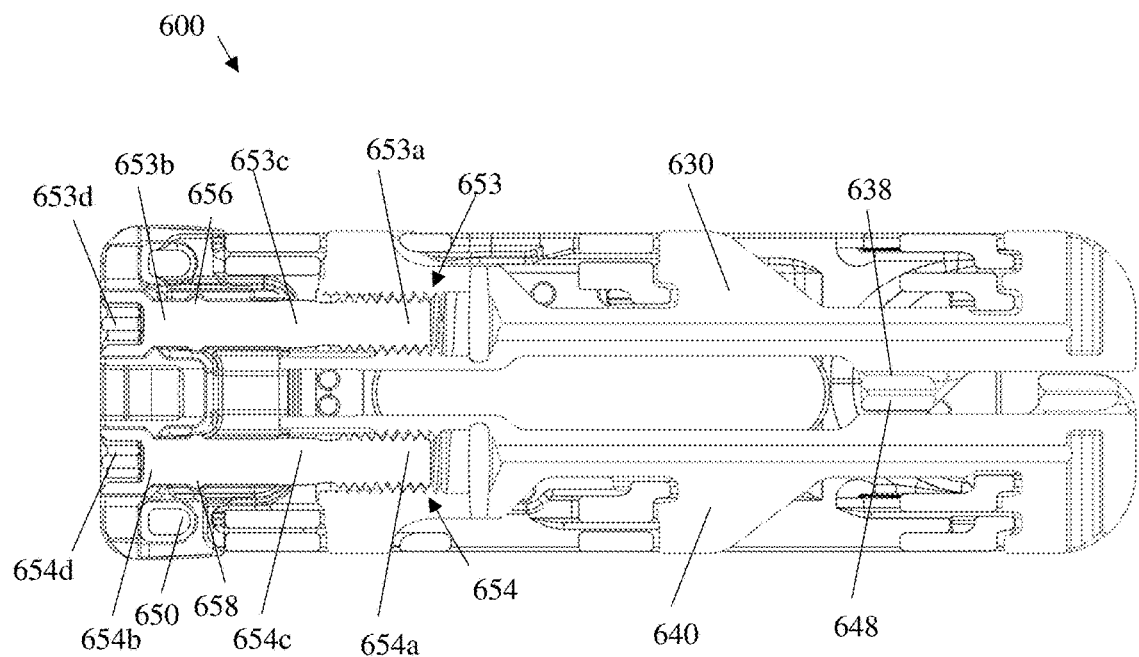
FIG. 32 shows a cross-sectional top view of the expandable implant in accordance with the fifth embodiment.
Figure 33:
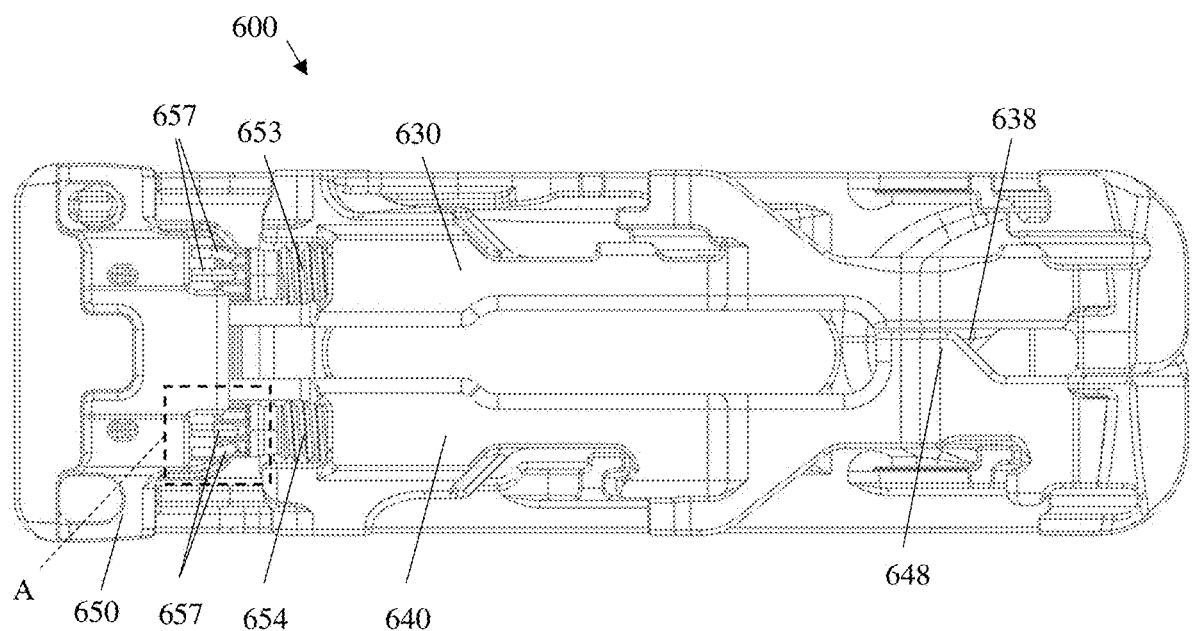
FIG. 33 shows a top-down view of the expandable implant in accordance with the fifth embodiment, with the top plate removed.
Figure 34:
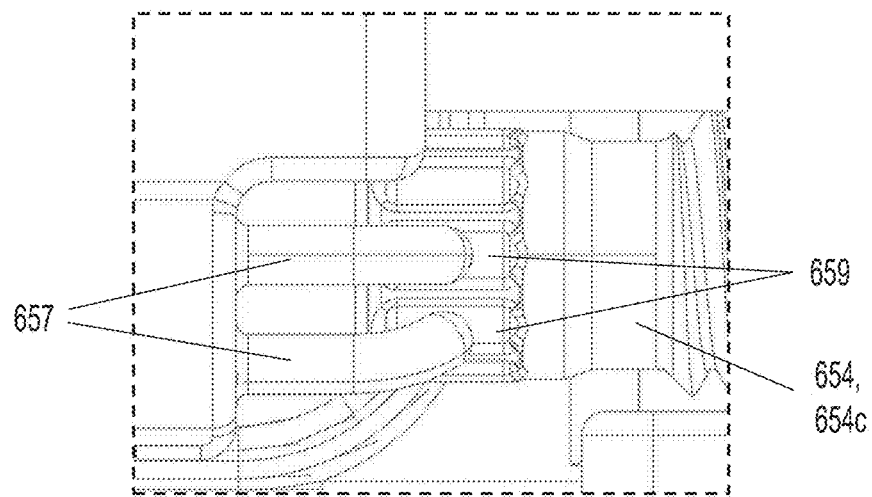
FIG. 34 shows an enlarged view of the box A of FIG. 33.

FIG. 31 is an exploded view of the expandable fusion intervertebral implant device 600 according to this embodiment. As best seen in FIG. 31, the expandable fusion intervertebral implant device 600 comprises a first endplate 610, a second endplate 620, a first expansion member 630, a second expansion member 640, a first actuator 653, a second actuator 654, and a housing 650.

The first endplate 610 has a top surface (or bone contacting surface) 612, an interior surface 614 opposite the top surface 612, a first side 615*a*, a second side 615*b*, a plurality of extensions 611*a* (FIG. 29) extending from the first side 615*a* along an edge of the endplate 610, and a plurality of extensions 611*b* (FIG. 30-31) extending from the second side 615*b* and offset from an edge of the endplate 610. The second endplate 620 has a bottom surface (or bone contacting surface) 622, an interior surface 624 opposite the bottom surface 622, a first side 625*a*, a second side 625*b*, a plurality of extensions 621*a* (FIG. 31) extending from the first side 625*a* offset from an edge of the endplate 620, and a plurality of extensions 611*b* (FIGS. 30-31) extending from the second side 625*b* along an edge of the endplate 620.

According to an exemplary embodiment, the first and second endplates 610, 620 are identical to each other in size and shape and are arranged opposite each other. According to an alternative embodiment, the first endplate 610 may have a height on the first side 615*a* that is greater than the height of the second side 615*b* of the first endplate 610 and/or greater than a maximum height of the second endplate 620. Each of the first and second endplates 610, 620 may further comprise openings 613, 623 (FIG. 31) extending from the top or bottom surface 612, 622 through the interior surface 614, 624 of the endplate 610, 620. According to one exemplary embodiment, each of the first and second endplates 610, 620 includes at least one central fusion aperture 613, 623, dimensioned and configured to allow bone growth through the first endplate 610, through a central region of the implant device 600 and through the second endplate 620. According to one embodiment best seen in FIG. 35, each of the first and second endplates 610, 620 comprises a porous bone contacting layer adjacent the top surface 612 and bottom surface 620, respectively.

The first expansion member 630 has a length comparable to the length of the first and second endplates 610, 620. The first expansion member 630 has a leading end 632, a trailing end 634, a plurality of curved surfaces 631 and an aperture 636 in the trailing end 634 that extends into at least a portion of the length of the first expansion member 630. The leading end 632 of the first expansion member 630 is beveled or tapered to assist with insertion of the expandable fusion intervertebral implant device 600 into an intervertebral space. The leading end 632 of the first extension member 630 extends beyond the leading ends 602 of the first and second endplates 610, 620 and forms the leading end of the overall expandable fusion intervertebral implant device 600. The leading end 632 of the first expansion member 630 may also comprise a dovetail or tongue and groove feature that mates with a corresponding feature on the first endplate 610. This dovetail or tongue and groove feature is configured to engage the corresponding feature on at least one of the first and second endplates 610, 620 to actively pull the first endplate 610 toward the second endplate 620 to "actively collapse" the expandable fusion intervertebral implant device 600.

According to an exemplary embodiment, the first expansion member 630 has a plurality of curved surfaces 631 that are spaced apart from each other and configured to engage the plurality of extensions 611a of the first side 615a of the first endplate 610 and the plurality of extensions 611a offset from the edge of the first side 625a of the second endplate 620. The first expansion member 630 may also comprise a cleat 638 (FIGS. 31-33) extending generally perpendicular to the longitudinal axis of the first expansion member 630 configured to mate with a corresponding cleat 648 (FIGS. 31-33) on the second expansion member 640 and allowing the first and second expansion members 630, 640 to be slidingly engaged with each other.

The second expansion member 640 includes features corresponding to the features described above with respect to first expansion member 630. That is, the second expansion member 640 has a leading end 642, a trailing end 644, a plurality of curved surfaces 641, an aperture 646 in the trailing end 644 that extends into at least a portion of the length of the second expansion member 640, and a cleat 648. The leading end 642 of the second expansion member 640 is beveled or tapered to assist with insertion of the expandable fusion intervertebral implant device 600 into an intervertebral space. The leading end 642 of the second extension member 640 extends beyond the leading ends 602 of the first and second endplates 610, 620 and forms the leading end of the overall expandable fusion intervertebral implant device 600. The leading end 642 of the second expansion member 640 may also comprise a dovetail or tongue and groove feature 633 (FIG. 35) that mates with a corresponding feature on the first endplate 610 and second endplate 620. This dovetail or tongue and groove feature 633 is configured to engage the corresponding feature on at least one of the first and second endplates 610, 620 to actively pull the first endplate 610 toward the second endplate 620 to "actively collapse" the expandable fusion intervertebral implant device 600.

Figure 35:
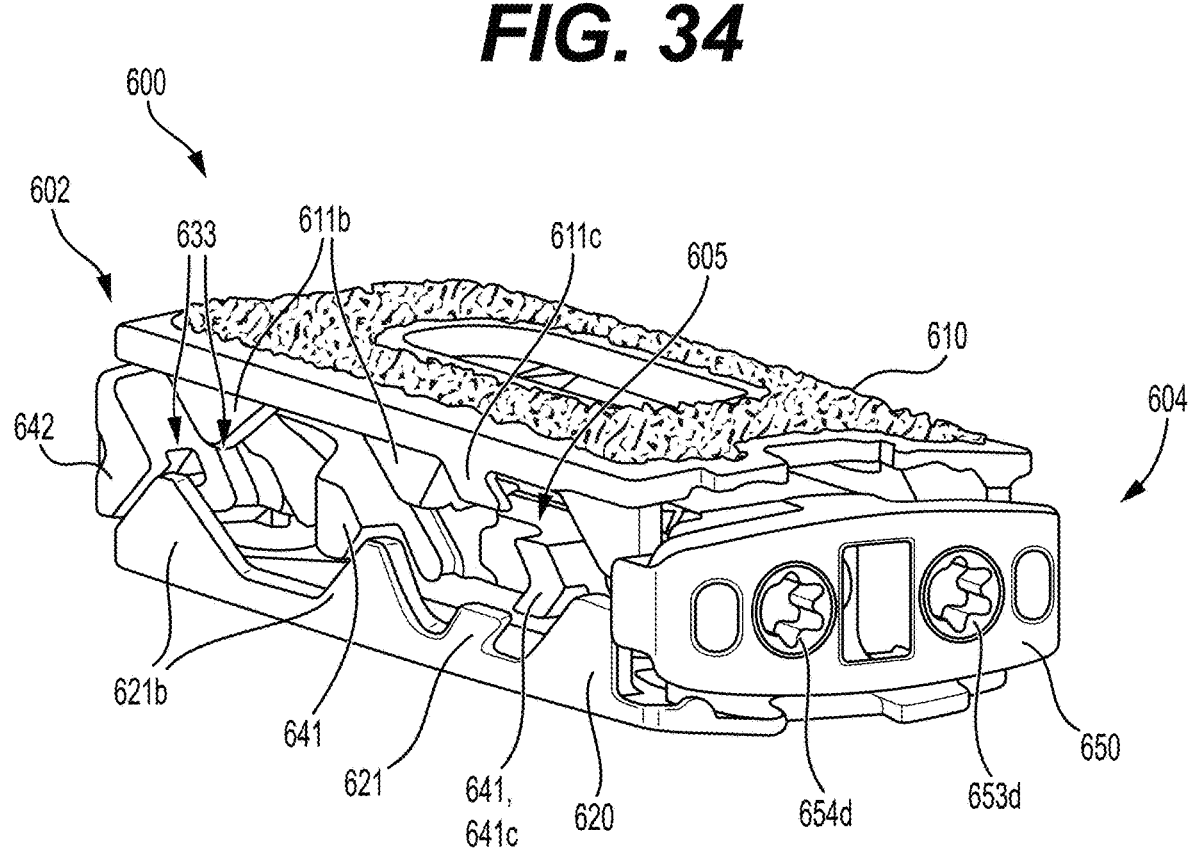
FIG. 35 shows a rear perspective view of the expandable implant in accordance with the fifth embodiment, the expandable implant having enhanced surface structure.

Shapes, geometries and/or configurations of one or more wedges 631, 641 of expansion members 630, 640 and wedges 611, 621 of endplates 610, 620 may be customized to enhance expansion and collapsing. For example, as shown in FIG. 35, another active collapse feature 605 is shown. Specifically, the first and second endplates 610, 620 may include at least one extension 611c, 621c that is configured to interact with a wedge 641c of an expansion member 630, 640 during collapsing of the implant 600 such that the interaction of the extension 611c, 621c of the first and second endplate 610, 620 with the wedge 641c of the expansion member 630, 640 directs and assists in collapsing of the implant 600. It is to be understood that endplates 610, 620 and expansion members 630, 640 may include any number of active collapse mechanisms without departing from aspects of the disclosure.

The curved surfaces 641 of the second expansion member 640 are configured to engage the extensions 611b offset from the edge of the second side 615b of the first endplate 610 and the extensions 621b along the edge of the second side 621b of the second endplate 620. According to one exemplary embodiment, the first and second expansion members 630, 640 are identical in size and shape and may be arranged opposite each other such that the leading end 632, 642 and trailing end 634, 644 of the first and second expansion members 630, 640 are side by side, but the second expansion member 640 is flipped about the longitudinal axis of the expansion member. According to an exemplary embodiment, the apertures 636, 646 at the trailing ends 634, 644 of the first and second expansion members 630, 640 are dimensioned to receive a first portion 653a, 654a of the first and second actuator 653, 654, respectively. The apertures 636, 646 may be threaded to correspond to a thread form on the first portion 653a, 654a of the first and second actuators 653, 654.

The first and second actuators 653, 654 each comprise a first portion 653a, 654a, a second portion 653b, 654b, and a middle region 653c, 654c (FIG. 32) between first portion 653a, 654a and the second portion (653b, 654b). According to an exemplary embodiment, the first and second actuators 653, 654 are identical to each other in size and shape. The first portions 653a, 654a of each of the first and second actuators 653, 654 are configured to engage the first and second expansion members 630, 640. For example, when the first actuator 653 is rotated in a first direction, the first expansion member 630 translates toward the housing 650 and when the first actuator 653 is rotated in a second direction, the first expansion member 630 translates away from the housing 650. Likewise, when the second actuator 654 is rotated in a first direction, the second expansion member 640 translates toward the housing 650 and when the second actuator 654 is rotated in a second direction, the second expansion member 640 translates away from the housing 650. The second portions 653b, 654b of each of the first and second actuators 653, 654 are substantially or completely captured within first and second apertures 652a, 652b (FIG. 31) in the housing 650, respectively. The trailing end of the second portion of each of the first and second actuators 653, 654 comprises an engagement feature 653d, 654d (FIG. 32), configured to receive the distal tip of an expansion driver that engages and rotates the first and second actuators 653, 654 in a first or a second direction. The engagement feature 653d, 654d at the trailing end of each of the first and second actuators 653, 654 is exposed through the corresponding aperture 652s, 652b in the housing 650 at the proximal face of the housing 650, which is also the trailing end face of the overall expandable fusion intervertebral implant device 600. Each of the actuators 653, 654 and corresponding expansion members 630, 640 may be completely independent of the other. The actuator 653, 654 and expansion member 630, 640 assemblies are configured to be actuated and translated independently, thereby increasing the height of only the first or the second side of the expandable fusion intervertebral implant device 600. Alternatively, the actuators 653, 654 may both be engaged and rotated simultaneously, causing parallel expansion of the expandable fusion intervertebral implant device 600. By way of example, the second portion 653b, 654b of each of the first and second actuators 653, 654 may include a lip or flange 656, 658 that has a greater circumference than the rest of the second portion 653b, 654b of the actuator 653, 654 that is retained in a corresponding pocket or channel within the first and second apertures 652a, 652b of the housing 650. The first and second actuators 653, 654 also each include a middle or central region 653c, 654c. The central region 653c, 654c may have a plurality of concave channels about the circumference of the middle region 653c, 654c of the actuator 653, 654.

Housing 650 is configured to be positioned at trailing end 604 of expandable fusion intervertebral implant device 600. According to one embodiment, the housing 650 has a width from the first side to the second side of the expandable fusion intervertebral implant device 600 that is equal to the maximum width of the expandable fusion intervertebral implant device 600. The housing 650 includes a distal face and a proximal face, first and second apertures 652a, 652b (FIG. 31) that extend from the proximal face through the distal face of the housing 650, and a plurality of flexible extensions 657 (FIG. 33) extending from the distal face of housing 650 adjacent the first and second apertures 652a, 652b. The first and second apertures 652a, 652b are configured to retain second portions 653b, 654b of first and second actuators 653, 654, respectively. Each of the plurality of flexible extensions 657 extending from the distal face of housing 650 has a distal end configured to rest in one of the lobes or concave channels 659 (FIG. 34) about the circumference of the middle region 653c, 654c of actuator 653, 654. According to an exemplary embodiment, the plurality of flexible extensions 657 may have different lengths, such that flexible extensions 657 engage concave channels 659 in the middle region 653c, 654c of actuator 653, 654 at different locations. According to the exemplary embodiment, housing 650, including the plurality of flexible extensions 657, may be of unitary construction. The flexible extensions 657 are configured to restrict an undesired movement of first and second actuators 653, 654. The second portions 653b, 654b of first and second actuators 653, 654 are captive within housing 650 without requiring the use of a secondary lock or screw feature.

According to an exemplary embodiment, the entire expandable fusion intervertebral implant device 600 may be manufactured using additive manufacturing techniques. According to another exemplary embodiment, the expandable fusion implant may comprise a biocompatible metal. At least one of the endplates 610, 620 or expansion members 630, 640 may be treated to enhance the surface structure to facilitate bone ingrowth or ongrowth to the treated component. According to another exemplary embodiment, the entire expandable fusion intervertebral implant device 600 may be treated to enhance the surface structure to facilitate bone ingrowth or ongrowth to the expandable fusion intervertebral implant device 600.

Figure 36:
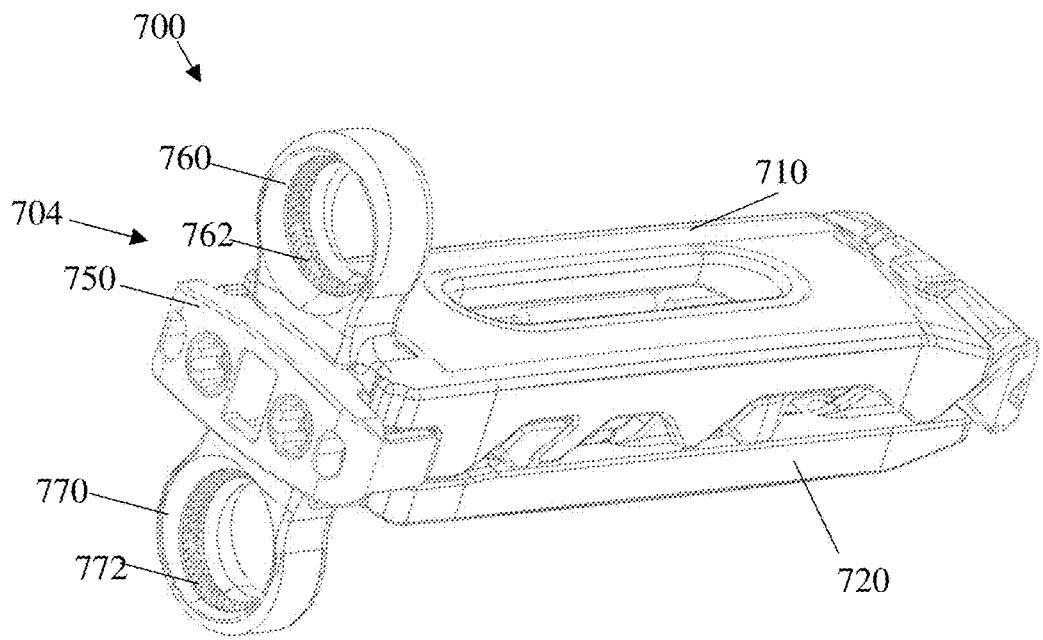
FIG. 36 shows a rear perspective side view of the expandable implant in accordance with a sixth embodiment, the expandable implant being plated.

Turning now to FIG. 36, another embodiment of an expandable fusion intervertebral implant device 700 is shown. This embodiment includes features having substantial correspondence with the features of expandable fusion intervertebral implant device 600 (FIGS. 29-35), however, expandable fusion intervertebral implant device 700 includes a plated design. More specifically, expandable fusion intervertebral implant device 700 includes at least one fixation aperture 760 integrally formed with the first endplate 710 and at least fixation aperture 770 integrally formed with the second endplate 720. Each of the at least one fixation apertures 760, 770 is configured to receive a fixation element, e.g., a bone screw, blade, etc. therein for affixing the expandable fusion intervertebral implant device 700 to adjacent bone. The housing 750 may be positioned between the at least one fixation aperture 760 integrally formed with the first endplate 710 and the at least one fixation aperture 770 integrally formed with the second endplate 770. While shown as including two fixation apertures 760, 770, it is understood that each endplate 710, 720 may include any number of fixation apertures without departing from aspects of the disclosure. Additionally, it is also contemplated that only one of the first endplate 710 or second endplate 720 may include a fixation aperture.

In this embodiment, each of the at least one fixation apertures 760, 770 are shown including a canted coil mechanism 762, 772 as an anti-back out feature, but other types may be used to secure the expandable fusion intervertebral implant device 700 with respect to adjacent bone once it is placed and sized. Additional details of an exemplary canted coil locking mechanism can be found in International Patent Application No. PCT/US2009/040396, filed on Apr. 13, 2009, and published as WO 2009/126968 A1 on Oct. 15, 2009, which is hereby incorporated by reference as if set forth in its entirety herein. For example, some embodiments may include a polymeric member for ultrasonic welding. Additional details of an exemplary polymeric member can be found in International Patent Application No. PCT/US2018/040463, filed on Jun. 29, 2018, and published as WO 2019/006407 A1 on Jan. 3, 2019, which is hereby incorporated by reference as if set forth in its entirety herein.

Each of the at least one fixation apertures 760, 770 may be positioned about the endplates 710, 720 on a trailing end 704 of the expandable fusion intervertebral implant device 700. Further, each of the at least one fixation apertures 760, 770 may be centered about the endplates 710, 720 at the trailing end 704 or may be positioned off-centered. Additionally, each of the at least one fixation apertures 760, 770 may be configured to direct a bone screw positioned therein in a desired angulation and direction. In one example, the fixation apertures 760, 770 are shifted to an anterior portion of the expandable fusion intervertebral implant device 700 and the bone screw trajectory may be directed in a posterior direction, which allows the expandable fusion intervertebral implant device 700 to be used in an anterior to psoas (ATP) approach.

Figure 37:
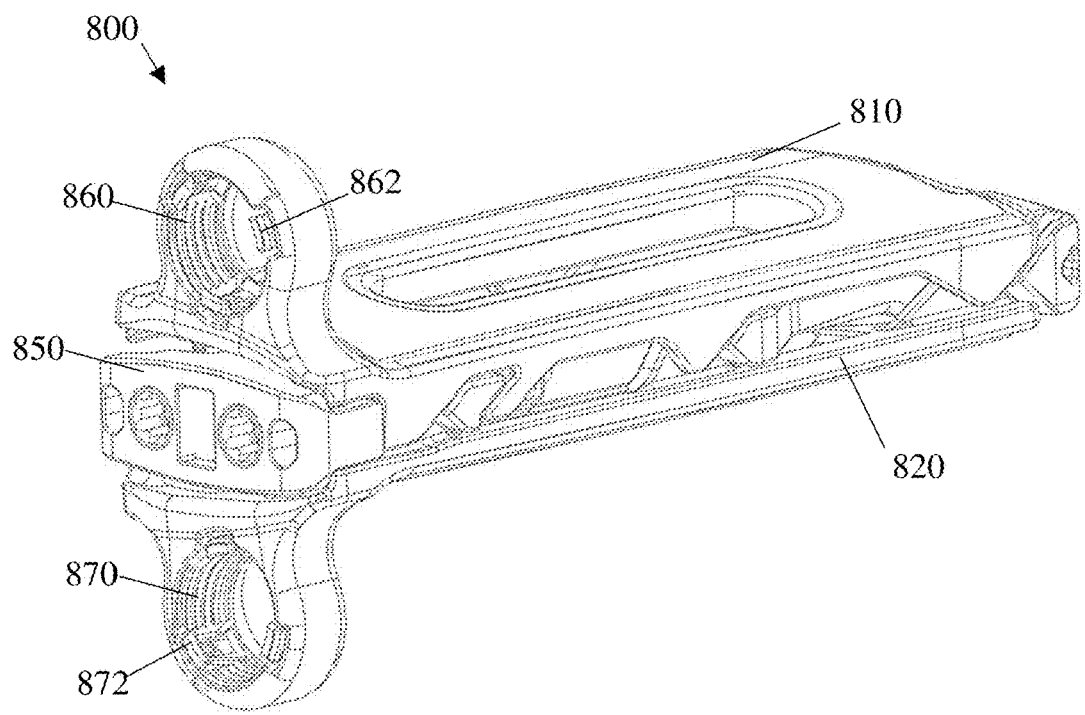
FIG. 37 shows perspective side view of the expandable implant in accordance with a seventh embodiment, the expandable implant being plated.

Turning now to FIG. 37, another embodiment of an expandable fusion intervertebral implant device 800 is shown. This embodiment includes features that substantially correspond to those described relative to expandable fusion intervertebral implant device 600 (FIGS. 29-35), however, expandable fusion intervertebral implant device 800 includes is plated in a manner similar to expandable fusion intervertebral implant device 700. More specifically, expandable fusion intervertebral implant device 800 includes at least one fixation aperture 860 integrally formed with the first endplate 810 and at least fixation aperture 870 integrally formed with the second endplate 820. Each of the at least one fixation apertures 860, 870 are configured to receive a fixation element, e.g., a bone screw, blade, etc., therein for affixing the expandable fusion intervertebral implant device 800 to adjacent bone. The housing 850 may be positioned between the at least fixation aperture 860 integrally formed with the first endplate 810 and the at least one fixation aperture 870 integrally formed with the second endplate 870.

Figure 38:
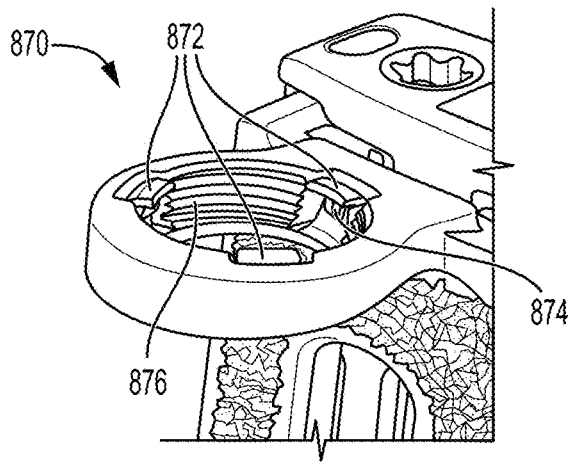
FIG. 38 shows an enlarged perspective view of the fixation aperture in accordance with an embodiment of the disclosure.
Figure 40:
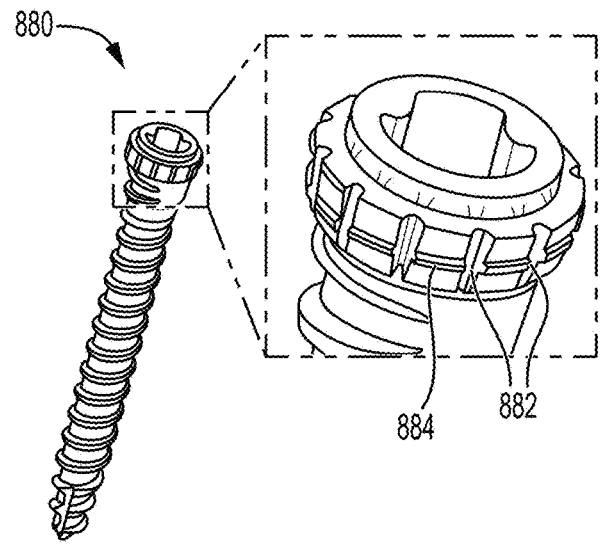
FIG. 40 shows a perspective view of a fixation element in accordance with an embodiment of the disclosure, including an enlarged view of the head of the fixation element.
Figure 39:
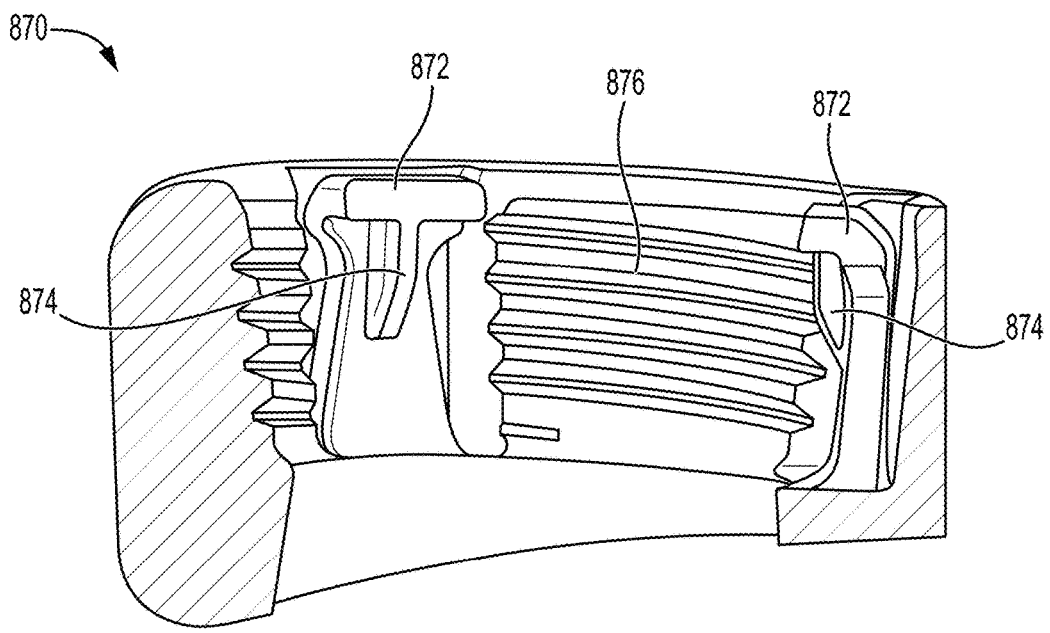
FIG. 39 shows a cross-sectional view of the fixation aperture of FIG. 38.

In this embodiment, each of the at least one fixation apertures 860, 870 are shown including at least one latch lock 862, 872 positioned therein. While the fixation apertures 860, 870 are shown including three latch locks 862, 872 per fixation aperture, it is to be understood that any number of latch locks 862, 872 may be included without departing from aspects of the disclosure. FIG. 38 shows an enlarged view of the fixation aperture 870 having latch locks 872 therein. FIG. 39 shows an enlarged cross-sectional view of the fixation aperture 870. As shown, each latch lock 872 includes a ratchet tab 874 for engaging scalloped cuts 882 (FIG. 40) on the head of a bone screw 880 (FIG. 40) thereby providing an anti-backout mechanism. The ratchet tabs 874 may project inwardly, toward the center of the fixation aperture 870 and/or distally (downwardly in the view as shown FIG. 39) toward the opposite end of the fixation aperture 870. The latch locks 872 may be configured to permit some degree of flexibility to allow the latch locks 872 to deflect or splay outwardly during bone screw 880 placement. Additionally, the fixation aperture 870 includes threads 876 for engaging a helical interface feature 884 on the head of the fixation element 880 to ensure bottoming out of the fixation element 880 within the fixation aperture 870. While the latch lock, ratchet tab, and threads 876 have been shown and described relative to the at least one fixation aperture 870, it is to be understood that the at least one fixation aperture 860 may include substantially the same features, and therefore description of which has been omitted for brevity. Latch locks 872, ratchet tabs 874, and threads 876 may be formed within the fixation aperture 870, and analogously within fixation aperture 860 via 3D printing.

In use, a fixation element 880 is inserted into a fixation aperture 860, 870 via a driver (not shown). As the fixation element 880 is inserted, the latch locks 872 deflect or splay outwardly and then snap back inwardly toward the center of the fixation aperture 860, 870 such that the rachet tab 874 of each latch lock 872 engages with a scalloped cut 882 of the fixation element 880, thereby providing rotational backout resistance. Additionally, the helical interface feature 884 of the fixation element 880 engages with threads 876 of the fixation aperture 860, 870, thereby providing a hard stop tactile feedback and backout resistance. Specifically, the helical interface feature 884 has a pitch that differs from the pitch of the threads 876 and causes cross-threading and/or binding to provide tactile feedback and ensure bottoming out of the fixation element 880 within the fixation aperture 860, 870.

Figure 41:
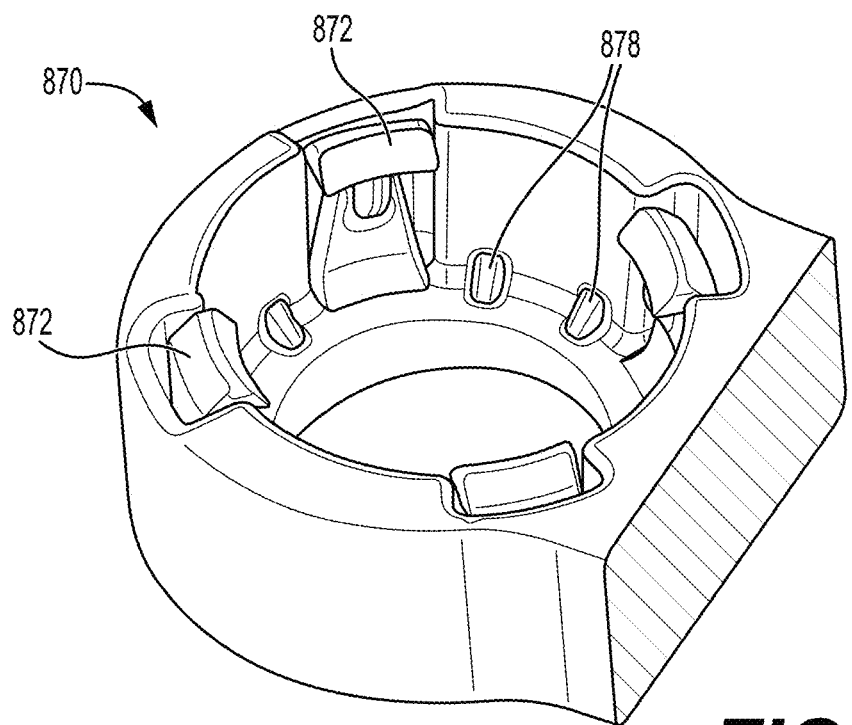
FIG. 41 shows a perspective top view of a fixation aperture according to another embodiment.

FIG. 41 shows another embodiment of anti-back out and hard stop features for the fixation apertures 860, 870. Specifically, this embodiment will again be discussed relative to fixation aperture 870 but is equally applicable to the fixation aperture 860. As shown, the fixation aperture 870 includes the latch locks 872 as in FIGS. 38-39, but instead of threads 876, includes ridges or bumps 878 may be formed proximate to the bottom of the fixation aperture 870 for mating with and/or engaging with cuts formed within the fixation element 880. The ridges or bumps 878 may be formed via 3D printing. The ridges or bumps 878 provide a hard stop in the form of a noticeable torque spike when the bottom of the head of the fixation element 880 engages with the ridges or bumps 878.

Figure 42:
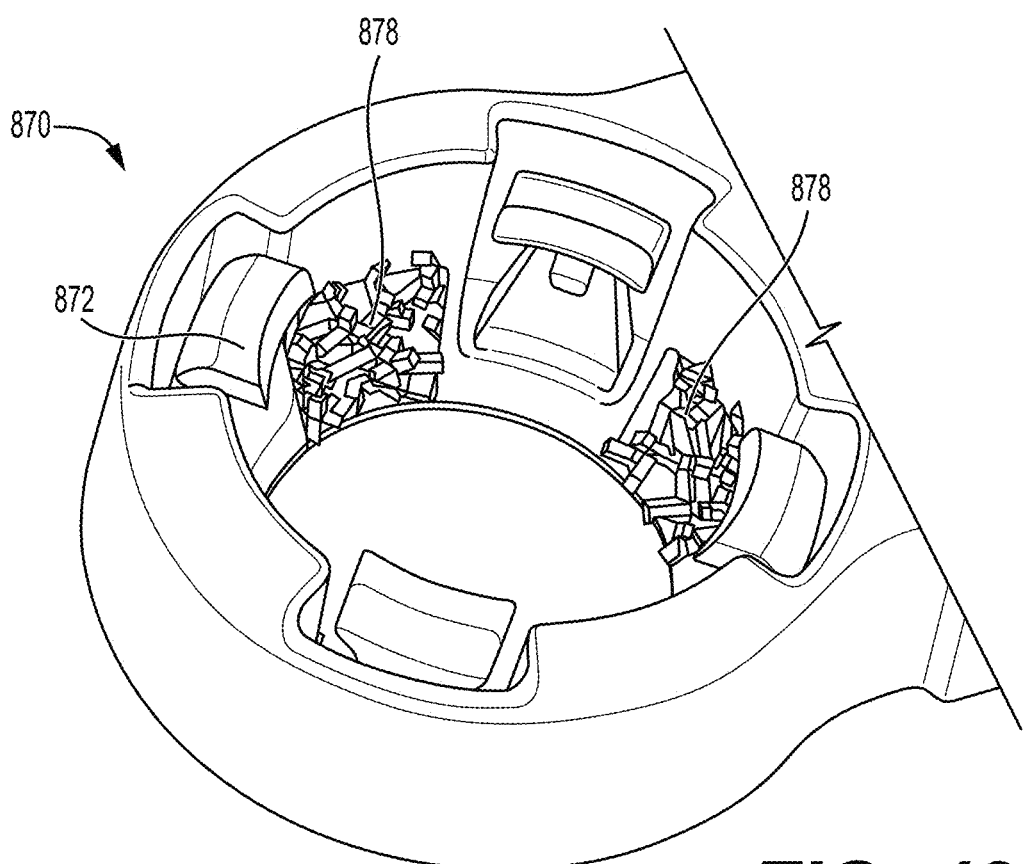
FIG. 42 shows a perspective top view of a fixation aperture according to another embodiment.
Figure 47:
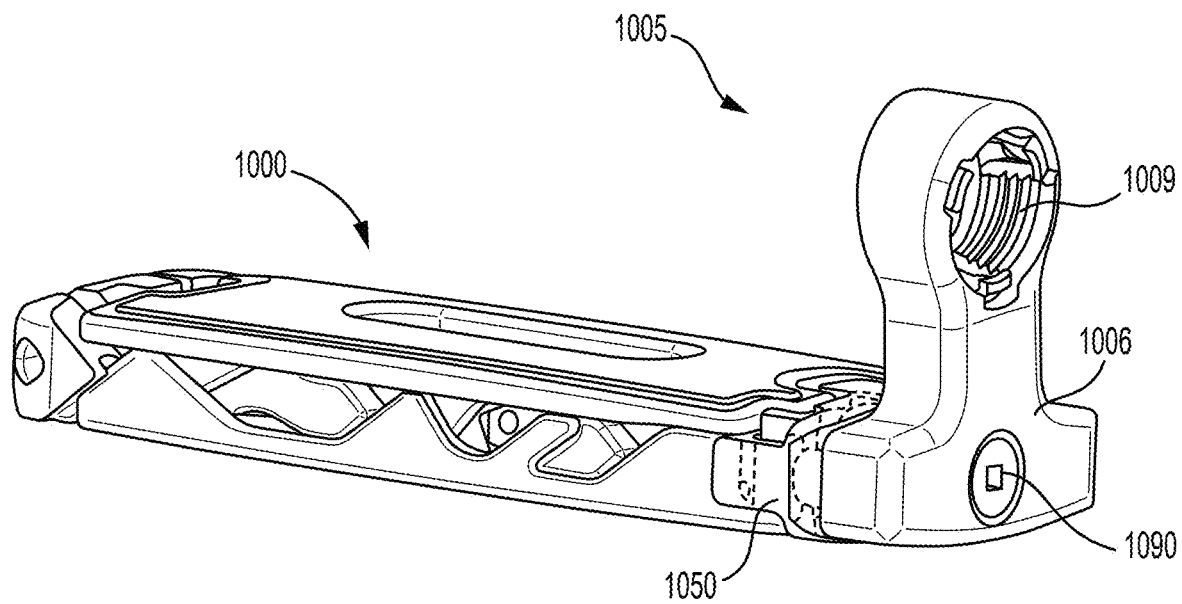
FIG. 47 shows a perspective side view of a modular plate design of an expandable implant in accordance with a ninth embodiment.
Figure 48:
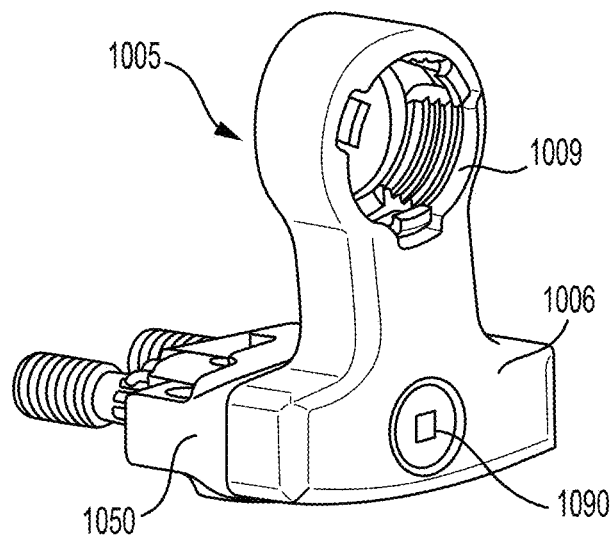
FIG. 48 shows a perspective side view of the modular plate coupled with the housing in accordance with the ninth embodiment.

FIG. 42 shows another embodiment of the ridges or bumps 878. In this embodiment, the ridges or bumps 878 are in the form of micropores formed via 3D printing. The micropores provide a hard stop in the form of a noticeable torque spike when the bottom of the screw head engages with the micropores.

FIGS. 43-45 show another embodiment of an anti-backout mechanism in the form of a washer 886 configured to be formed substantially surrounding the head of the fixation element 880 and being received within a groove around the head. The washer 886 includes a helical interface feature 884. The helical interface feature of the washer 886 is configured to engage threads 876 (FIGS. 38-39) of the fixation aperture 870 similar to that described relative to FIG. 40. An inner surface of the washer 886 may be keyed and dimensioned such that sufficient counter torque to seat the fixation element 880 is provided by preventing rotation. This configuration allows the fixation element 880 to be driven into the fixation apertures of the expandable fusion intervertebral implant device 700, 800 and achieve a hard stop, but allows for toggle to account for post-operative settling of the bone screw 880. The fixation element 880 having washer 886 may be formed via 3D printing.

FIG. 46 shows an embodiment of an expandable fusion intervertebral implant device 900 including fixation apertures 960, 970 integrally formed with endplates 910, 920 wherein the fixation apertures 960, 970 are positioned on the trailing end 904 at the anterior side and configured to provide a screw trajectory toward the posterior side. Such an embodiment may be used in an anterior to psoas (ATP) approach.

Figure 49:
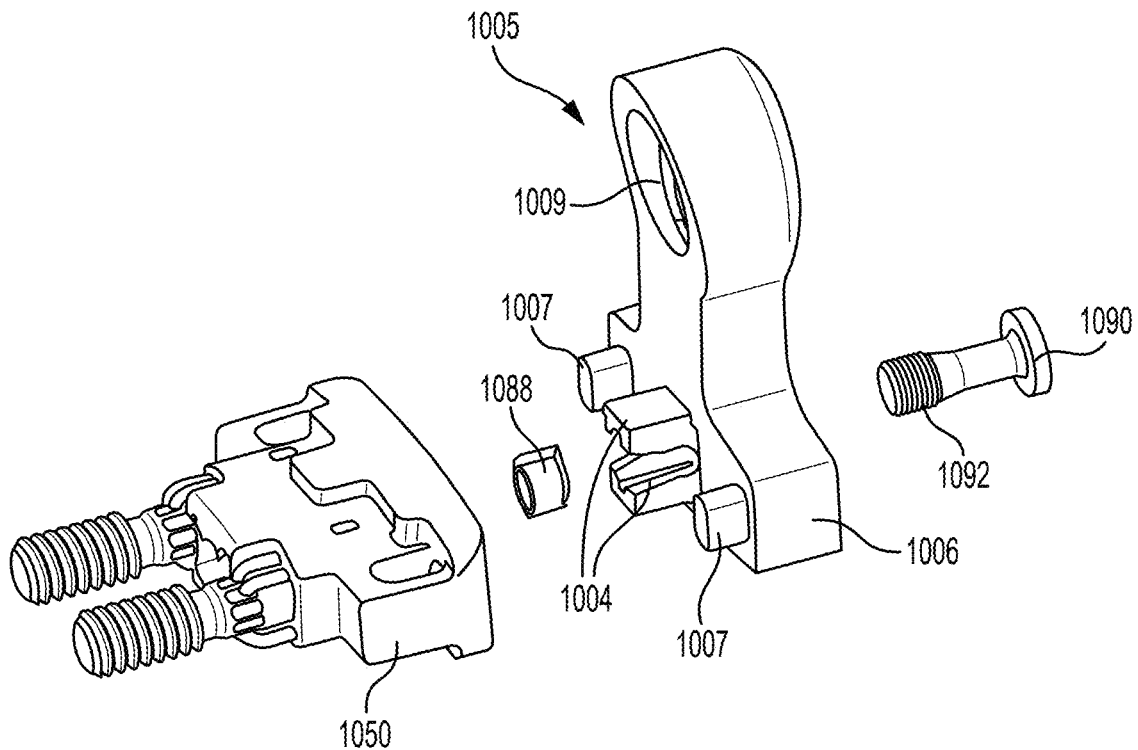
FIG. 49 shows an exploded view of the modular plate with the housing in accordance with the ninth embodiment.
Figure 50:
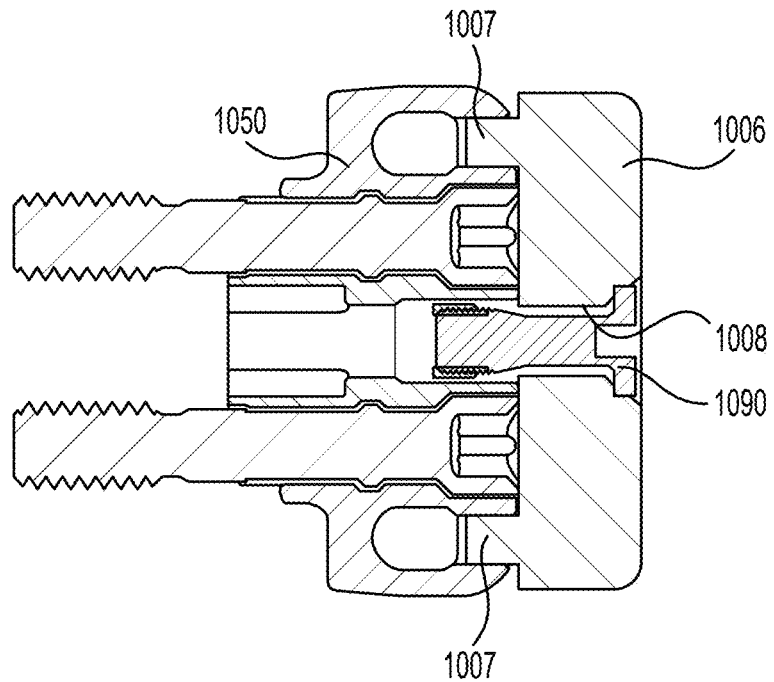
FIG. 50 shows a cross-sectional top view of the modular plate coupled with the housing in accordance with the ninth embodiment.
Figure 51:
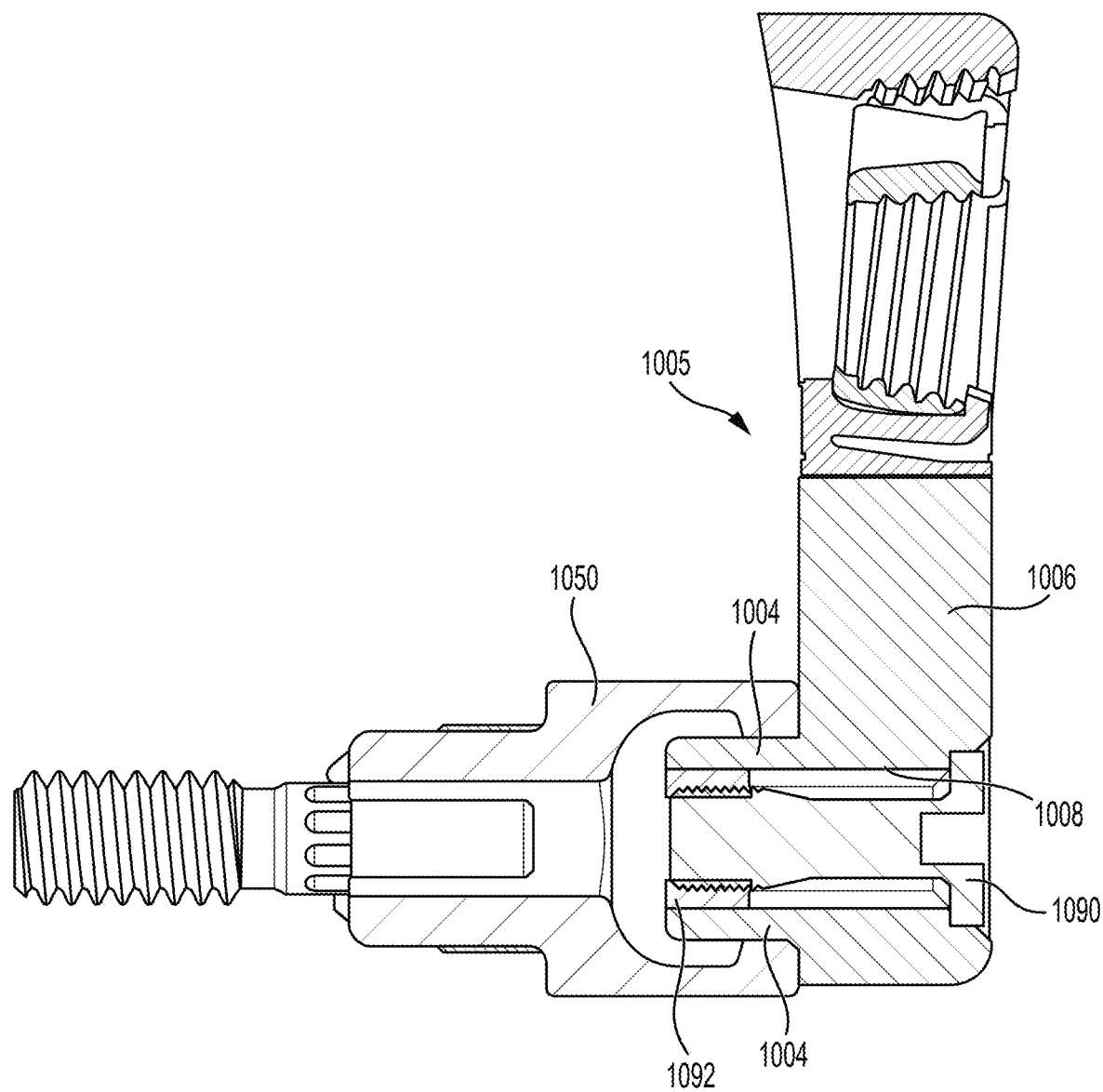
FIG. 51 shows a cross-sectional side view of the modular plate coupled with the housing in accordance with the ninth embodiment.

Turning now to FIGS. 47-51, an expandable fusion intervertebral implant device 1000 having a modular plate configuration is shown. Specifically, implant device 1000 is shown including a plate 1005 configured to be coupled to the housing 1050 of the expandable fusion intervertebral implant device 1000. The expandable fusion intervertebral implant device 1000 may be in the form of any of the embodiments discussed herein, e.g., shown in FIGS. 1-37. Plate 1005 includes a main body 1006 having at least one boss, tab, extension, and/or protrusion (hereinafter, "boss") 1007 extending from a distal surface thereof (FIGS. 49-50). Boss 1007 is configured to be received within an aperture within the housing 1050. Main body 1006 also includes a pair of wings, tabs, extensions, or protrusions (hereinafter, "wings") 1004 which also extend into an opening within the housing 1050. Main body 1006 may be substantially "T-shaped" or "t-shaped", however, other shapes are also feasible and contemplated by the disclosure. The main body 1006 may also have an opening 1008 extending entirely through the main body 1006 and may be configured to be aligned with an aperture within the housing 1050.

Plate 1005 may also include at least one fixation aperture 1009 that is integrally formed with the main body 1006. Fixation aperture 1009 is configured to receive a fixation element, e.g., a bone screw, a blade, etc., therein to fix the plate 1005, and therefore, the expandable fusion intervertebral implant device 1000, to adjacent bone. The fixation aperture 1009 may be configured similarly to any of fixation apertures 760, 770, 860, 870, 960, 970 (FIGS. 36-46) such that fixation aperture 1009 may include any number of anti-backout mechanisms and bottom out feedback mechanisms, including a canted coil mechanism, a latch lock mechanism, threads, ridges, bumps, and/or micropores as described herein.

An attachment 1090 may be configured for insertion into opening 1008 (FIG. 50) of main body 1006 and into the opening within housing 1050 to fix plate 1005 to expandable fusion intervertebral implant device 1000. In some embodiments, attachment 1090 includes a threaded end 1092 configured to threadably engage with a complementary thread within the opening of housing 1050. In other embodiments, attachment 1090 is threaded within a nut 1092 positioned within and between wings 1004 of plate 1006. As attachment 1090 is threaded into opening 1008, nut 1092 is drawn away from housing 1050, thereby causing wings 1004 to separate and/or spread apart. As a result, an interference fit is created between wings 1004 and housing 1050.

The embodiment shown in FIGS. 47-51 is modular in that the plate 1005 is separate but couplable and removeable relative to the expandable fusion intervertebral implant device 1000. The plate 1005 is configured to be removeably coupled to housing 1050 after expandable fusion intervertebral implant device 1000 is expanded to a desired configuration. As a result, the method described herein may also include coupling the plate 1005 to the implant and fixing the plate 1005 to bone via a fixation element received within fixation aperture 1009. This modular design allows the surgeon the option of using a plated implant without the need to remove a non-plated implant and replacing it with a plated implant.

Although particular features and embodiments have been described in an effort to enable those with skill in the art to make and use the claimed invention, it should be understood that several variations, alterations or substitutions can be achieved to arrive at the present disclosure. Nothing in this description shall be construed as limiting the spirit and scope of the invention as set forth in the claims, below.

What is claimed is:

1. An expandable implant comprising:
a first endplate and a second endplate;
an actuator housing disposed between the first and second endplates, and having first and second through holes;
a first actuator rotatably disposed in the first through hole and having a first shaft including a non-threaded portion and a threaded portion extending from the non-threaded portion;
a second actuator rotatably disposed in the second through hole and having a second shaft including a non-threaded portion and a threaded portion extending from the non-threaded portion of the second shaft;
a first translating member threadably receiving the threaded portion of the first actuator, the first actuator having a plurality of first divots circumferentially disposed around the non-threaded portion of the first shaft;
a second translating member threadably receiving the threaded portion of the second actuator, the second actuator having a plurality of second divots circumferentially disposed around the non-threaded portion of the second shaft;
a plurality of flexible members configured to selectively engage the first actuator or the second actuator to maintain the first actuator or the second actuator in a selected rotational position;
wherein the first translating member is configured to move independently from the second translating member;
wherein the first translating member and the second translating member are configured to change a spatial relationship between the first endplate and the second endplate, and
wherein each flexible member is an elongated member having a proximal portion and a distal portion, each proximal portion being disposed on the housing and each distal portion configured to engage one of the plurality of first divots or one of the plurality of second divots.

2. The expandable implant of claim 1, wherein at least one of the first endplate and the second endplate further comprise a porous bone engagement surface.

3. The expandable implant of claim 1, wherein at least one of the first translating member and the second translating member further comprise at least one wedge configured to interface with at least one of the first endplate and the second endplate.

4. The expandable implant of claim 1, wherein the first translating member is moveably coupled to the second translating member.

5. The expandable implant of claim 4, wherein the first translating member is moveably coupled to the second translating member by a dovetail coupling.

6. The expandable implant of claim 1, wherein each of the plurality of flexible members are shaped to nest within a respective divot on the non-threaded portion of the first actuator or the second actuator.

7. An expandable implant comprising:
a first endplate and a second endplate;
an actuator housing disposed between the first and second endplates, and having first and second through holes;
a first drive screw rotatably disposed in the first through hole and having a first shaft including a non-threaded portion and a threaded portion extending from the non-threaded portion;
a second drive screw rotatably disposed in the second through hole and having a second shaft including a non-threaded portion and a threaded portion extending from the non-threaded portion of the second shaft;
a first translating member disposed between the first endplate and the second endplate and threadably receiving the threaded portion of the first drive screw;
a second translating member disposed between the first endplate and the second endplate and threadably receiving the threaded portion of the second drive screw; and
a plurality of flexible members configured to selectively engage the first drive screw or the second drive screw to maintain the first drive screw or the second drive screw in a selected rotational position,
wherein the first translating member is configured to move independently from the second translating member,
wherein the first translating member and the second translating member are configured to change a spatial relationship between the first endplate and the second endplate, and
wherein each flexible member is an elongated member having a proximal portion and a distal portion, each proximal portion being disposed on the housing and each distal portion configured to engage one of a plurality of divots circumferentially disposed on the first drive screw or the second drive screw.

8. The expandable implant of claim 7, wherein at least one of the first endplate and the second endplate further comprise a porous bone engagement surface.

9. The expandable implant of claim 7, wherein the first translating member further comprises at least one wedge.

10. The expandable implant of claim 7, wherein the second translating member further comprises at least one wedge.

11. The expandable implant of claim 7, wherein the first translating member is moveably coupled to the second translating member.

12. The expandable implant of claim 11, wherein the first translating member is moveably coupled to the second translating member by a dovetail.

13. The expandable implant of claim 7, wherein each of the plurality of flexible members are each shaped to nest within a respective divot on the non-threaded portion of the first drive screw or the second drive screw.

14. A method of treating a spinal deformity, comprising the steps:

accessing an intervertebral disc space via a lateral approach;

inserting an expandable implant into the intervertebral disc space, the expandable implant having a first endplate, a second endplate, an actuator housing disposed between the first and second endplates, and having first and second through holes, a first actuator rotatably disposed in the first through hole and having a first shaft including a non-threaded portion and a threaded portion extending from the non-threaded portion, a second actuator rotatably disposed in the second through hole and having a second shaft including a non-threaded portion and a threaded portion extending from the non-threaded portion of the second shaft, a first translating member threadably receiving the threaded portion of the first actuator, a second translating member threadably receiving the threaded portion of the second actuator, with the first translating member and the second translating member configured to change a spatial relationship between the first endplate and the second endplate as they move, and a plurality of flexible members configured to selectively engage the first actuator or the second actuator;

actuating at least one of the first actuator and the second actuator to change the spatial relationship between the first endplate and the second endplate, thereby changing a dimension of the expandable implant; and engaging the first actuator or the second actuator with the plurality of flexible members to maintain the first actuator or the second actuator in a selected rotationally position, wherein each flexible member is an elongated member having a proximal portion and a distal portion, each proximal portion being disposed on the housing and each distal portion configured to engage a corresponding one of a plurality of first divots or one of a plurality of second divots circumferentially disposed on the first and second non-threaded portions of the first and second shafts.

* * * * *